(12) United States Patent  (10) Patent No.: US 8,236,339 B2
Motterlini et al.  (45) Date of Patent: Aug. 7, 2012

(54) THERAPEUTIC DELIVERY OF CARBON MONOXIDE

(75) Inventors: Roberto Angelo Motterlini, Middlesex (GB); Brian Ernest Mann, Sheffield (GB)

(73) Assignee: hemoCORM Limited, London (GB)

( * ) Notice: Subject to any disclaimer, the term of this patent is extended or adjusted under 35 U.S.C. 154(b) by 75 days.

(21) Appl. No.: 11/275,780

(22) Filed: Jan. 27, 2006

(65) Prior Publication Data

US 2006/0115542 A1 Jun. 1, 2006

Related U.S. Application Data

(62) Division of application No. 10/143,824, filed on May 14, 2002, now Pat. No. 7,045,140.

(30) Foreign Application Priority Data

May 15, 2001 (GB) .................................... 0111872

(51) Int. Cl.
A61F 2/02 (2006.01)
(52) U.S. Cl. ...................................................... 424/423
(58) Field of Classification Search .................. None
See application file for complete search history.

(56) References Cited

U.S. PATENT DOCUMENTS

| | | |
|---|---|---|
| 2,870,180 A | 1/1959 | Kozikowski et al. |
| 3,278,570 A | 10/1966 | Wilkinson et al. |
| 3,694,232 A | 9/1972 | Hall et al. |
| 3,812,166 A | 5/1974 | Wiechert |
| 3,829,504 A | 8/1974 | Hall et al. |
| 3,980,583 A | 9/1976 | Mitchell et al. |
| 4,189,487 A | 2/1980 | Klosa |
| 4,312,989 A | 1/1982 | Spielvogel et al. |
| 4,322,411 A | 3/1982 | Vinegar et al. |
| 4,535,167 A | 8/1985 | Freidinger |
| 4,613,621 A | 9/1986 | Horrmann |
| 4,649,151 A | 3/1987 | Dougherty et al. |
| 4,657,902 A | 4/1987 | Kappas et al. |
| 4,668,670 A | 5/1987 | Rideout et al. |
| 4,699,903 A | 10/1987 | Rideout et al. |
| 4,709,083 A | 11/1987 | Spielvogel |
| 4,910,211 A | 3/1990 | Imamura et al. |
| 4,938,949 A | 7/1990 | Borch et al. |
| 5,010,073 A | 4/1991 | Kappas et al. |

(Continued)

FOREIGN PATENT DOCUMENTS

DE 4014762 A1 11/1991
(Continued)

OTHER PUBLICATIONS

Motterlini et al "Carbon Monoxide-releasing Molecules Characterization of Biochemical and Vascular Activities", Circulation Research, Feb. 8, 2002.*

(Continued)

*Primary Examiner* — Carlos Azpuru
(74) *Attorney, Agent, or Firm* — Wolf, Greenfield & Sacks, P.C.

(57) ABSTRACT

Metal carbonyls are used to deliver CO having biological activity, for example vasodilatation and inhibition of transplant rejection. The metal of the carbonyl is typically of groups 7 to 10, e.g. Fe and Ru. The carbonyl preferably has one or store ligands other than CO, such as amine acids, to modulate the CO release property and solubility.

11 Claims, 17 Drawing Sheets

Iron pentacarbonyl
[Fe(CO)₅]

Dimanganese decacarbonyl
[Mn₂(CO)₁₀]

U.S. PATENT DOCUMENTS

| | | | |
|---|---|---|---|
| 5,086,060 A | 2/1992 | Haley et al. |
| 5,102,670 A | 4/1992 | Abraham et al. |
| 5,254,706 A | 10/1993 | Spielvogel et al. |
| 5,312,816 A | 5/1994 | Spielvogel et al. |
| 5,350,767 A | 9/1994 | Hallberg et al. |
| 5,447,939 A | 9/1995 | Glasky et al. |
| 5,621,000 A | 4/1997 | Arena et al. |
| 5,631,284 A | 5/1997 | Legzdins et al. |
| 5,659,027 A | 8/1997 | Spielvogel et al. |
| 5,664,563 A | 9/1997 | Schroeder et al. |
| 5,670,664 A | 9/1997 | Kao et al. |
| 5,700,947 A | 12/1997 | Soldato |
| 5,756,492 A | 5/1998 | Buelow et al. |
| 5,767,157 A | 6/1998 | Van Moerkerken |
| 5,801,184 A | 9/1998 | Glasky et al. |
| 5,811,463 A | 9/1998 | Legzdins et al. |
| 5,824,673 A | 10/1998 | Abrams et al. |
| 5,861,426 A | 1/1999 | Del Soldato et al. |
| 5,882,674 A | 3/1999 | Hermann |
| 5,885,621 A | 3/1999 | Head et al. |
| 5,888,982 A | 3/1999 | Perrella et al. |
| 5,891,689 A | 4/1999 | Takle et al. |
| 6,025,376 A | 2/2000 | Laurent et al. |
| 6,025,394 A | 2/2000 | Menander et al. |
| 6,027,936 A | 2/2000 | Glasky |
| 6,040,341 A | 3/2000 | Del Soldato et al. |
| 6,051,576 A | 4/2000 | Ashton et al. |
| 6,060,467 A | 5/2000 | Buelow et al. |
| 6,066,333 A | 5/2000 | Willis et al. |
| 6,177,471 B1 | 1/2001 | Menander et al. |
| 6,203,991 B1 | 3/2001 | Nabel et al. |
| 6,211,233 B1 | 4/2001 | Del Soldato |
| 6,218,417 B1 | 4/2001 | Del Soldato |
| 6,242,432 B1 | 6/2001 | del Soldato |
| 6,251,927 B1 | 6/2001 | Lai et al. |
| 6,284,752 B1 | 9/2001 | Abrams et al. |
| 6,331,564 B1 | 12/2001 | Brugnara et al. |
| 6,338,963 B1 | 1/2002 | Glasky et al. |
| 6,344,178 B1 | 2/2002 | Alberto et al. |
| 6,350,752 B1 | 2/2002 | Glasky et al. |
| 6,417,182 B1 | 7/2002 | Abrams et al. |
| 6,518,269 B1 | 2/2003 | Camden et al. |
| 6,645,938 B2 * | 11/2003 | Oeltgen et al. ............... 514/13 |
| 6,673,908 B1 | 1/2004 | Stanton, Jr. |
| 7,011,854 B2 | 3/2006 | Haas et al. |
| 7,045,140 B2 | 5/2006 | Motterlini et al. |
| 7,053,242 B1 | 5/2006 | Alberto et al. |
| 7,964,220 B2 | 6/2011 | Haas et al. |
| 7,968,605 B2 | 6/2011 | de Matos et al. |
| 7,989,650 B2 | 8/2011 | Motterlini et al. |
| 2002/0043595 A1 | 4/2002 | Bridgers et al. |
| 2002/0045611 A1 | 4/2002 | Abrams et al. |
| 2002/2045611 | 4/2002 | Bridger et al. |
| 2002/0155166 A1 | 10/2002 | Choi et al. |
| 2002/0165242 A1 | 11/2002 | Glasky et al. |
| 2002/0193363 A1 | 12/2002 | Bridger et al. |
| 2003/0039638 A1 | 2/2003 | Bach et al. |
| 2003/0064114 A1 | 4/2003 | Motterlini et al. |
| 2003/0068387 A1 | 4/2003 | Buelow et al. |
| 2003/0124157 A1 | 7/2003 | Engles et al. |
| 2003/0157154 A1 | 8/2003 | Fuller et al. |
| 2003/0207786 A1 | 11/2003 | Miracle et al. |
| 2003/0219496 A1 | 11/2003 | Otterbein et al. |
| 2003/0219497 A1 | 11/2003 | Otterbein et al. |
| 2004/0052866 A1 | 3/2004 | Otterbein et al. |
| 2004/0067261 A1 | 4/2004 | Haas et al. |
| 2004/0122091 A1 | 6/2004 | Dasseux et al. |
| 2004/0131602 A1 | 7/2004 | Buelow et al. |
| 2004/0143025 A1 | 7/2004 | Buelow et al. |
| 2004/0214900 A1 | 10/2004 | Forbes et al. |
| 2004/0228930 A1 | 11/2004 | Billiar et al. |
| 2004/0258772 A1 | 12/2004 | Otterbein et al. |
| 2005/0048133 A1 | 3/2005 | Pinsky et al. |
| 2005/0175555 A1 | 8/2005 | Stradi et al. |
| 2006/0127501 A1 | 6/2006 | Motterlini et al. |
| 2006/0147548 A1 | 7/2006 | Motterlini et al. |
| 2006/0148900 A1 | 7/2006 | Haas et al. |
| 2006/0233890 A1 | 10/2006 | Haas et al. |
| 2007/0065485 A1 | 3/2007 | Motterlini et al. |
| 2007/0207217 A1 | 9/2007 | Haas et al. |
| 2007/0207993 A1 | 9/2007 | Haas et al. |
| 2007/0219120 A1 | 9/2007 | De Matos et al. |
| 2008/0026984 A1 | 1/2008 | De Matos et al. |
| 2010/0105770 A1 | 4/2010 | Motterlini et al. |
| 2010/0196516 A1 | 8/2010 | Nobre |
| 2011/0015263 A1 | 1/2011 | Motterlini et al. |
| 2011/0038955 A1 | 2/2011 | Rodrigues et al. |

FOREIGN PATENT DOCUMENTS

| | | |
|---|---|---|
| EP | 0 034 238 | 8/1981 |
| EP | 0076493 A2 | 4/1983 |
| EP | 0 181 721 | 5/1986 |
| EP | 0 632 026 A | 1/1995 |
| FR | 2816212 A1 | 5/2002 |
| GB | 1107510 A | 3/1968 |
| GB | 0111872.8 A | 7/1968 |
| GB | 0227135.1 A | 4/1994 |
| GB | 0227138.5 A | 4/1994 |
| GB | 2395431 A | 5/2004 |
| GB | 2395432 A | 5/2004 |
| HU | 211 084 B | 4/1990 |
| HU | 57595 A2 | 12/1991 |
| WO | WO-85/04326 A1 | 10/1985 |
| WO | WO 91/01128 | 2/1991 |
| WO | WO 91/01301 | 2/1991 |
| WO | WO-92/03402 A1 | 3/1992 |
| WO | WO-92/04905 A1 | 4/1992 |
| WO | WO 93/05795 | 4/1993 |
| WO | WO 94/01413 A | 1/1994 |
| WO | WO 94/22482 | 10/1994 |
| WO | WO 95/05814 | 3/1995 |
| WO | WO-95/09831 | 4/1995 |
| WO | WO-95/35105 A1 | 12/1995 |
| WO | WO-96/03125 | 2/1996 |
| WO | WO-96/09038 | 3/1996 |
| WO | WO-97/16405 A1 | 5/1997 |
| WO | WO-97/36615 A1 | 10/1997 |
| WO | WO-97/37644 A1 | 10/1997 |
| WO | WO 98/09618 A2 | 3/1998 |
| WO | WO 98/29115 | 7/1998 |
| WO | WO-98/38179 A1 | 9/1998 |
| WO | WO 98/48848 | 11/1998 |
| WO | WO-99/67231 A1 | 12/1999 |
| WO | WO-00/10613 A2 | 3/2000 |
| WO | WO 00/21965 A1 | 4/2000 |
| WO | WO-00/36113 A2 | 6/2000 |
| WO | WO 00/56145 | 9/2000 |
| WO | WO 00/56743 | 9/2000 |
| WO | WO-00/61537 A2 | 10/2000 |
| WO | WO 01/12584 A2 | 2/2001 |
| WO | WO 01/16359 | 3/2001 |
| WO | WO 01/25243 A | 4/2001 |
| WO | WO-01/28545 A2 | 4/2001 |
| WO | WO 02/078684 | 10/2002 |
| WO | WO 02/080923 | 10/2002 |
| WO | WO-02/092072 A2 | 11/2002 |
| WO | WO 02/092075 | 11/2002 |
| WO | WO 03/000114 | 1/2003 |
| WO | WO 03/066067 | 8/2003 |
| WO | WO-03/067598 A2 | 8/2003 |
| WO | WO 03/072024 | 9/2003 |
| WO | WO-03/082850 A1 | 10/2003 |
| WO | WO 03/088923 | 10/2003 |
| WO | WO 03/088981 | 10/2003 |
| WO | WO 03/094932 | 11/2003 |
| WO | WO-03/096977 A2 | 11/2003 |
| WO | WO-03/103585 A2 | 12/2003 |
| WO | WO-2004/029033 A1 | 4/2004 |
| WO | WO-2004/043341 A2 | 5/2004 |
| WO | WO-2004/045598 A1 | 6/2004 |
| WO | WO-2004/045599 A1 | 6/2004 |
| WO | WO-2004/080420 A2 | 9/2004 |
| WO | WO-2005/013691 A1 | 2/2005 |
| WO | WO-2005/090400 A1 | 9/2005 |
| WO | WO-2006/012215 A1 | 2/2006 |
| WO | WO-2007/073226 A1 | 6/2007 |
| WO | WO-2007/085806 A2 | 8/2007 |

| WO | WO-2008/003953 A2 | 1/2008 |
| WO | WO-2008/069688 A2 | 6/2008 |
| WO | WO-2008/130261 A1 | 10/2008 |
| WO | WO-2009/013612 A1 | 1/2009 |

OTHER PUBLICATIONS

Dharmaraj et al., Ruthenium (II) complexes containing bidentate Schiff bases and their antifungal activity. Transition Metal Chemistry. 2001; 26(1-2): 105-109.

Lipmann et al., Organometallic Lewis Acids. LI. Reactivity of organometallic Lewis Acids (OC)4Re(OEt2)FBF3 and (OC)2(PPh3)2Ru(FBF3)2. Journal of Organometallic Chemistry. 1994;466(1-2):167-174.

Severin et al., Metal complexes of biologically important ligands. LXX. Synthesis, stereochemistry and reactions of ruthenium (II) and osmium (II) complexes with .alpha.-amino carboxylates. 1994; 127(4): 615-620.

Viswanathamurthi et al., Synthesis, characterization and biocidal studies of ruthenium (II) carbonyl complexes containing tetradentate Schiff bases. Transition Metal Chemistry. 1999; 24(6):638-641.

Beutler, The effect of carbon monoxide on red cell life span in sickle cell disease. Blood. Aug. 1975;46(2):253-9.

Brashears et al., Effect of meat packaging technologies on the safety and spoilage-indicating characteristics of ground beef—Phase 1: safety characteristics. 2006. National Cattleman's Beef Asscoiation. 22 pages. Available at www.fda.gov/ohrms/dockets/dockets/05p0459/05p-0459-c000009-01-vol2.pdf.

Brüne et al., Inhibition of platelet aggregation by carbon monoxide is mediated by activation of guanylate cyclase. Mol Pharmacol. Oct. 1987;32(4):497-504.

Coville et al., Steric measurement of substituted cyclopentadiene ligands and the synthesis and proton NMR spectral analysis of [(.eta. 5-C5H4R)Fe(CO)(L)I] complexes with variable R. Organometallics. 1992;11(3):1082-90.

Kamimura et al., The protective effect of carbon monoxide on the ischemia-induced cell death. The J Biochem. Aug. 2002;74(8):926. Japanese abstract. English translation provided.

McLaughlin et al., Potentiation of carbon monoxide-induced relaxation of rat aorta by YC-1 [3-(5'-hydroxymethyl-2'-furyl)-1-benzylindazole]. Can J Physiol Pharmacol. Apr. 2000;78(4):343-9.

Skattebøl et al., Synthesis of (±)-Lineatin, an aggregation pheromone component of Trypodendron lineatum. Acta Chem Scand B. 1985;39:291-304.

Tamaki, Role of second messenger gases in ischemia and reperfusion injury. Low Temp Med. 2001;27(1):1-5. English abstract provided.

Tsuburai et al., The role of heme oxygenase in pulmonary circulation. Low Temp Med. 2001;27(1):25-35. English abstract provided.

Vulapalli et al., Cardioselective overexpression of HO-1 prevents I/R-induced cardiac dysfunction and apoptosis. Am J Physiol Heart Circ Physiol. Aug. 2002;283(2):H688-94.

Yet et al., Cardiac-specific expression of heme oxygenase-1 protects against ischemia and reperfusion injury in transgenic mice. Circ Res. Jul. 20, 2001;89(2):168-73.

Rutkowska-Zbik et al., Theoretical density functional theory studies on interactions of small biologically active molecules with isolated heme group. J Comput Chem. Mar. 2007;28(4):825-31.

Salazar-Salinas et al., Molecular biosensor based on a coordinated iron complex. J Chem Phys. Mar. 14, 2009;130(10):105101.

Motterlini, R. et al.; "Characterization of vasoactive effects elicited by carbon monoxide-releasing molecules."; Journal of Vascular Research, Abstracts, 8th International Symposium on Mechanisms of Vasodilation; May 31-Jun. 3, 2001; 055.

Durante W.; "Heme Oxygenase-1 in Growth Control and its Clinical Application to Vascular Disease"; J. Cell. Physiol.; 2003; 195; 373-82.

Gordeuk, V. P. et al; "Carbonyl Iron Therapy for Iron Deficiency Anemia"; Blood; 1986; 67(3); 745-752.

Huebers, H. A. et al.; "Absorption of carbonyl iron"; J. Lab. Clin. Med.; 1986; 108; 473-8.

Sacks, P. V. et al.; "Comparative bioavailability of elemental iron powders for repair of iron deficiency anemia in rats. Studies of efficacy and toxicity of carbonyl iron"; The American Journal of Clinical Nutrition; 1978; 31;566-73.

Furchgott, et al, Blood Vessels 1991;28:52-61 "Endothelium-Dependent and -Independent Vasodilation Involving Cyclic GMP: Relaxation Induced by Nitric Oxide, Carbon Monoxide and Light".

Wang et al, Biochemistry, vol. 18, No. 22, 1979, 4960-4977 "A Correlation of the Visible and Soret Spectra of Dioxygen- and Carbon Monoxide-Heme Complexes and Five-Coordinate Heme Complexes with the Spectra of Oxy-, Carboxy-, and Deoxyhemoglobins".

Schubert, Nov. 1933 Carbon Monoxide on Iron and Cobalt Cysteine Complexes, vol. 55, 4563-4570 "The Action of Carbon Monoxide on Iron and Cobalt Complexes of Cysteine".

Carroll et al, Can. J. Chem. vol. 52, 1974, 1914-1922 "Ligand Abstraction in the Reaction of Aryldiazonium Ions with some Iron Complexes Containing Coordinated Cysteine, Maleonitriledithiol, or Triarylphosphine".

Sjöstrand, Scan. J. Clin. Lab Invest., 1949, 1:201-214 "Endogenous Formation of Carbon Monoxide in Man Under Normal and Pathological Conditions".

Coburn et al, J. of Clinical Investigation, vol. 42, No. 7, 1963, 1172-1178 "Endogenous Carbon Monoxide Production in Man".

Tenhunen et al, J. of Biological Chemistry, vol. 244, No. 23, 6388-6394 (1969) "Microsomal Heme Oxygenase".

Maines, Dept. of Biophysics, University of Rochester, FASEB J 2:2557-2568 (1988) "Heme oxygenase: function, multiplicity, regulatory mechanisms, and clinical applications".

Morita et al, Proc. Natl. Acad. Sci. USA, Cell Biology, 1995, vol. 92, 1475-1479, "Smooth muscle cell-derived carbon monoxide is a regulator of vascular cGMP".

Sammut et al, British J. of Pharmacology, 1998, 125, 1437-1444 "Carbon monoxide is a major contributor to the regulation of vascular tone in aortas expressing high levels of haeme oxygenase-1".

Maines, Annu. Rev., Pharmacol. Toxocol, 1997, 517-554, "The Heme Oxygenase System: A Regulator of Second Messenger Gases".

Soares et al, Nature Medicine, vol. 4, No. 9, 1998, 1073-1077, "Expression of heme oxygenase-1 can determine cardiac xenograft survival".

Willis et al, Nature Medicine, vol. 2, No. 1, 1996, 87-90 "Heme oxygenase: A novel target for the modulation of the inflammatory response".

Motterlini et al, Regulation of Pressor Responses by HO-1-Derived CO, 1998, 568-577 "Heme Oxygenase-1-Derived Carbon Monoxide Contributes to the Suppression of Acute Hypertensive Responses in Vivo".

Otterbein et al, Am. J. Physiol., 1999, 688-694 Carbon monoxide provides protection against hyperoxic lung injury.

Otterbein et al, J. Clin. Invest., 103; 1047-1054, 1999, "Exogenous administration of heme oxygenase-1 by gene transfer provides protection against hyperoxia-induced lung injury".

Herrick et al, Inorg. Chem. 1984, 23, 4550-4553 "Flash Photolytic Investigation of Photoinduced Carbon Monoxide Dissociation from Dinuclear Manganese Carbonyl Compounds".

Alessio et al, Inorg. Chem., 1995, 34, 4722-4734 "Carbonyl Derivatives of Chloride-Dimethyl Sulfoxide-Ruthenium (II) Complexes: Synthesis, Structural Characterization, and Reactivity of $RU(CO)_x(DMSO)_{4-x}Cl_2$ Complexes (x=1-3)".

Sato et al, The J. of Immunology, 2001, 4185-4195, "Carbon Monoxide Generated by Heme Oxygenase-1 Suppresses the Rejection of Mouse-to-Rat Cardiac Transplants".

Pneumatikakis et al, Inorganica Chimica Acta, 151, 1988, 243-248 "Interactions of Bis-[µ-chloro-chlorotricarbonylruthenium(II) and poly-[µ-dichloro-dicarbonylruthenium (II) with Nucleotides".

Yan et al, Pharmazie, 2000, 55(4), 307-313 "Cytotoxicity of rhenium (I) alkoxo and hydroxo carbonyl complexes in murin and human tumor cells".

Becker et al, Medical Sciences (1979), vol. 15, No. 2, 147-150, "Age related changes in antibody dependent cell mediated cytotoxicity in mouse spleen".

Nagai et al., Biochemistry, 1991, vol. 30, No. 26, 6495-6503, "Unusual CO Bonding Geometry in Abnormal Subunits of Hemoglobin M Boston and Hemoglobin M Saskatoon".

Tomita et al., Inorganic and Nuclear Chemistry Letters 1968, vol. 4, 715-718 "Structure and Reaction of Bis(L-cysteinato)Dicarbonyliron(II)".

Ferrier et al, J. of Molecular Structure 344, 1995, 189-193 "FTIR spectrometric study of geometrical isomers of dicarbonyl ferrobiscysteinate Influence of the counter cation".

Szakács-Schmidt et al, Inorganica Chimica Acta, 198-200, 1992, 401-405 "Iron (II) thiolates as reversible carbon monoxide carriers".

Takács et al, Inorganic Chimica Acta, 166, 1989, 39-46 "Synthesis and Molecular Structure of Carbonyl Derivatives of Iron(II) Thiolates Containing Nitrogen-donor Ligands".

Tomita et al, Inorg. Nucl. Chem. Letters vol. 4, 715-718, 1968, "Structure and Reaction of Bis(L-cysteinato)DicarbonylironII)".

Huang et al, J. Am. Chem. Soc., 1991, 113, 9141-9144 "Photolysis of the Histidine-Heme-CO Complex".

Silver et al, Inorganica Chimica Acta, 91, 1984, 279-283 "Mossbauer Studies on Protoprophyrin IX Iron(II) Solutions Containing Sulphur Ligands and their Carbonyl Adducts. Models for the Active Site of Cytochromes P-450".

Diamantis et al, Inorg. Chem., 1981, 20, 1141-1150 Preparation and Structure of Ethylenediaminetetraacetate Complexes of Ruthenium(II) with Dinitrogen, Carbon Monoxide, and other $\pi$-Acceptor Ligands.

Urban et al, J. Of Organometallic Chemistry 517, 1996, 191-200 Metal complexes of biologically important ligands, LXXXVII $\alpha$-Amino carboxylate complexes of palladium(II), iridium(III) and ruthenium(II) from chloro-bridged ortho-metallated metal compounds and $[((OC)_3Ru(Cl)(\mu-Cl)]_2$.

Motterlini et al, Carbon Monoxide-Releasing Molecules: Characterization of Biomedical and Vascular Activities, Circulation Research. 2002, vol. 90, No. 2, 1-8.

File Wrapper of U.S. Appl. No. 10/535,226 obtained from PTO IFW on Sep. 19, 2007.

File Wrapper of U.S. Appl. No. 10/567,157 obtained from PTO IFW on Sep. 19, 2007.

File Wrapper of U.S. Appl. No. 10/535,508 obtained from PTO IFW on Sep. 19, 2007.

Maines MD. The heme oxygenase system: a regulator of second messenger gases. Annu Rev Pharmacol Toxicol. 1997;37:517.

Verma A, Hirsch DJ, Glatt CE, Ronnett GV, Snyder SH. Carbon monoxide: a putative neural messenger. Science. 1993;259:381.

Sacerdoti D, Escalante B, Abraham NG, McGiff JC, Levere RD, Schwartzman ML. Treatment with tin prevents the development of hypertension in spontaneously hypertensive rats. Science. 1989;243:388.

Marks GS, Brien JF, Nakatsu K, McLaughlin BE. Does carbon monoxide have a physiological function? Trends Pharmacol Sci. 1991;12:185.

Coceani F, Kelsey L, Seidlitz E, Marks GS, McLaughlin BE, Vreman HJ, Stevenson DK, Rabinovitch M, Ackerley C. Carbon monoxide formation in the ductus arteriosus in the lamb: implications for the regulation of muscle tone. Br J Pharmacol. 1997;120:599.

Johnson RA, Colombari E, Colombari DSA, Lavesa M, Talman WT, Nasjletti A. Role of endogenous carbon monoxide in central regulation of arterial pressure. Hypertension. 1997;30:962.

Wang R, Wang ZZ, Wu LY. Carbon monoxide.

Suematsu M, Goda N, Sano T, Kashiwagi S, Egawa T, Shinoda Y, Ishimura Y. Carbon monoxide: an endogenous modulator of sinusoidal tone in the perfused rat liver. J Clin Invest. 1995;96:2431.

Morita T, Mitsialis SA, Koike H, Liu YX, Kourembanas S. Carbon monoxide controls the proliferation of hypoxic vascular smooth muscle cells. J Biol Chem. 1997;272:32804.

Otterbein LE, Bach FH, Alam J, Soares M, Tao Lu H, Wysk M, Davis RJ, Flavell RA, Choi AM. Carbon monoxide has anti-inflammatory effects involving the mitogen-activated protein kinase pathway. Nat Med. 2000;6:422-8.

Brouard S, Otterbein LE, Anrather J, Tobiasch E, Bach FH, Choi AM, Soares MP. Carbon monoxide generated by heme oxygenase 1 suppresses endothelial cell apoptosis. J Exp Med. 2000;192:1015.

Song R, Mahidhara RS, Liu F, Ning W, Otterbein LE, Choi AM. Carbon monoxide inhibits human airway smooth muscle cell proliferation via mitogen.

Fujita T, Toda K, Karimova A, Yan SF, Naka Y, Yet SF, Pinsky DJ. Paradoxical rescue from ischemic lung injury by inhaled carbon monoxide driven by derepression of fibrinolysis. Nat Med. 2001;7:598.

Foresti R, Motterlini R. The heme oxygenase pathway and its interaction with nitric oxide in the control of cellular homeostasis. Free Rad Res. 1999;31:459.

Otterbein LE. Carbon monoxide: innovative anti.

Chauveau C, Bouchet D, Roussel JC, Mathieu P, Braudeau C, Renaudin K, Tesson L, Soulillou JP, Iyer S, Buelow R, Anegon I. Gene transfer of heme oxygenase.

Motterlini R, Foresti R, Green CJ. Studies on the development of carbon monoxide.

Clark JE, Naughton P, Shurey S, Green CJ, Johnson TR, Mann BE, Foresti R, Motterlini R. Cardioprotective actions by a water-soluble carbon monoxide-releasing molecule. Circ Res. 2003;93:e2-e8.

Johnson TR, Mann BE, Clark JE, Foresti R, Green CJ, Motterlini R. Metal carbonyls: a new class of pharmaceuticals? Angew Chem Int Ed Engl. 2003;in press.

Motterlini R, Mann BE, Johnson TR, Clark JE, Foresti R, Green CJ. Bioactivity and pharmacological actions of carbon monoxide-releasing molecules. Curr Pharm Des. 2003;in press.

Waibel R, Alberto R, Willuda J, Finnern R, Schibli R, Stichelberger A, Egli A, Abram U, Mach JP, Pluckthun A, Schubiger PA. Stable one-step technetium-99m labeling of His-tagged recombinant proteins with a novel Tc(I)-carbonyl complex. Nat Biotechnol. 1999;17:897-901.

Egli A, Alberto R, Tannahill L, Schibli R, Abram U, Schaffland A, Waibel R, Tourwe D, Jeannin L, Iterbeke K, Schubiger PA. Organometallic 99mTc-aquaion labels peptide to an unprecedented high specific activity. J Nucl Med. 1999;40:1913-1917.

Alberto R, Schibli R, Egli A, Schubiger AP, Abram U, Kaden TA. A novel organometallic aqua complex of technetium for the labeling of biomolecules: Synthesis of [Tc-99m(OH2)(3)(CO)(3)](+) from [(TcO4)-Tc-99m](−) in aqueous solution and its reaction with a bifunctional ligand. J Am Chem Soc. 1998;120:7987-7988.

Alberto R, Ortner K, Wheatley N, Schibli R, Schubiger AP. Synthesis and properties of boranocarbonate: a convenient in situ CO source for the aqueous preparation of [(99m)Tc(OH(2))3(CO)3]+. J Am Chem Soc. 2001;123:3135-3136.

Abraham NG, Drummond GS, Lutton JD, Kappas A. The biological significance and physiological role of heme oxygenase. Cell Physiol Biochem 1996;6:129-68.

Soares MP, Lin Y, Anrather J, Csizmadia E, Takigami K, Sato K, Grey ST, Colvin RP, Choi AM, Poss KD, et al. Expression of heme oxygenase-1 can determine cardiac xenograft survival. Nature Med 1998;4:1073-7.

Hancock WW, Buelow R, Sayegh MH, Turka LA. Antibody-induced transplant arteriosclerosis is prevented by graft expression of anti-oxidant and anti-apoptotic genes. Nature Med 1998;4:1392-6.

Clark JE, Foresti R, Sarathchandra P, Kaur H, Green CJ, Motterlini R. Heme oxygenase-1-derived bilirubin ameliorates post-ischemic myocardial dysfunction. Am J Physiol Heart Circ Physiol 2000;278:H643-51.

Willis D, Moore AR, Frederick R, Willoughby DA. Heme oxygenase: a novel target for the modulation of inflammatory response. Nature Med 1996;2:87-90.

Bauer M, Pannen BHJ, Bauer I, Herzog C, Wanner GA, Hanselmann R, Zhang JX, Clemens MG, Larsen R. Evidence for a functional-link between stress-response and vascular control in hepatic portal circulation. Am J Physiol 1996;271:G929-35.

Fukuda K, Panter SS, Sharp FR, Noble LJ. Induction of heme oxygenase-1 (HO-1) after traumatic brain injury in the rat. Neurosci Lett 1995;199:127-30.

Yet SF, Pellacani A, Patterson C, Tan L, Folta SC, Foster L, Lee WS, Hsieh CM, Perrella MA. Induction of heme oxygenase-1 expression in vascular smooth muscle cells. A link to endotoxic shock. J Biol Chem 1997;272:4295-301.

Otterbein LE, Kolls JK, Mantell LL, Cook JL, Alam J, Choi AMK. Exogenous administration of heme oxygenase-1 by gene transfer provides protection against hyperoxia-induced lung injury. J Clin Invest 1999;103:1047-54.

Iris H. Hall et al. "The anti-inflammatory activity of boron derivatives in rodents". Metal Based Drugs, 2(1), 1-12, 1995.

Wu, L. et al.; "Different mechanisms underlying the stimulation of K(Ca) channels by nitric oxide and carbon monoxide."; J. Clin. Invest.; 2002; 110; 691-700.

Yachie, A. et al.; "Oxidative stress causes enhanced endothelial cell injury in human heme oxygenase-1 deficiency"; J. Clin. Invest.; 1999; 103; 129-35.

Friebe A, Mullershausen F, Smolenski A, Walter U, Schultz G and Koesling D. YC-1 potentiates nitric oxide- and carbon monoxide-induced cyclic GMP effects in human platelets. Mol Pharmacol 54: 962-967, 1998.

Friebe A, Schultz G and Koesling D. Sensitizing soluble guanylyl cyclase to become a highly CO-sensitive enzyme. Embo J 15: 6863-6868, 1996.

Moncada S, Palmer RMJ and Higgs EA. Nitric oxide: physiology, pathophysiology, and pharmacology. Pharmacol Rev 43: 109-142, 1991.

Stone JR and Marietta MA. Soluble guanylate cyclase from bovine lung: activation with nitric oxide and carbon monoxide and spectral characterization of the ferrous states. Biochemistry 33: 5636-5640, 1994.

Becker EM et al. NO-independent regulatory site of direct sGC stimulators like YC-1 and BAY 41-2272. BMC Pharmacology 1: 13, 2001.

Kharitonov, V. G. et al.; "Kinetics and Equilibria of Soluble Guanylate Cyclase Ligation by CO: Effect of YC-1"; Biochemistry; 1999; 38; 10699-706.

MEDLINE abstract, Diabetes, 2002, 51(4), 994-999.

Motterlini R, Foresti R, Green CJ. "Studies on the development of carbon monoxide-releasing molecules: potential applications for the treatment of cardiovascular dysfunction. In: Carbon Monoxide and Cardiovascular Functions." Wang R, ed. Oct. 30, 2001. CRC Press, Boca Raton, Florida.

Wang R, Wang ZZ, Wu LY. "Carbon monoxide-induced vasorelaxation and the underlying mechanisms", British Journal of Pharmacology (1997) 121, 927-934.

Song R, Mahidhara RS, Liu F, Ning W, Otterbein LE, Choi AM. Carbon monoxide inhibits human airway smooth muscle cell proliferation via mitogen-activated protein kinase pathway American Journal of Respiratory Cell and Molecular Biology, vol. 27 (2002) pp. 603-610.

Otterbein LE. Carbon monoxide: innovative anti-inflammatory properties of an age-old gas molecule Antioxidants & Redox Signaling, vol. 4, No. 2, 2002.

[No Author Listed] Biosis Chem Abstracts Database. Accession No. PREV200600414130. 2005. Otterbein et al., Cell Mol Biol (Noisy-le-grand). Oct. 3, 2005;51(5):433-40. Abstract.

[No Author Listed] Chemical Abstracts. 2004;141:270758. (Ryter et al.).

[No Author Listed] Chemical Abstracts. 2004;142:211995. (Stein et al.).

Abel et al., Anionic halogenopentacarbonyls of chromium, molybdenum, and tungsten. J Chem Soc. 1963:2068-70.

Abel et al., Carbonyl halides of manganese and some related compounds. J Chem Soc. 1959; Part 2:1501-5.

Abel et al., Reaction of molybdenum carbonyl with various halides: a potassium etherate salt. Chem Indust. 1960;442.

Adkison et al., Semicarbazone-based inhibitors of cathepsin K, are they prodrugs for aldehyde inhibitors? Bioorg Med Chem Lett. Feb. 15, 2006 15;16(4):978-83. Epub Nov. 15, 2005. Abstract only.

Akamatsu et al., Heme oxygenase-1-derived carbon monoxide protects hearts from transplant associated ischemia reperfusion injury. FASEB J. Apr. 2004;18(6):771-2. Epub Feb. 20, 2004.

Alessio et al., Carbonyl Derivatives of Chloride-Dimethyl Sulfoxide-Ruthenium(III) Complexes: Synthesis, Crystal Structure, and Reactivity of [(DMSO)2H][trans-RuCl4(DMSO-O)(CO)]and mer,cis-RuCl3(DMSO-O)2(CO). Inorg Chem. 1995;34(19):4716-21.

Allanson et al., Ultraviolet A (320-400 nm) modulation of ultraviolet B (290-320 nm)-induced immune suppression is mediated by carbon monoxide. J Invest Dermatol. Mar. 2005;124(3):644-50.

Allardyce et al., Development of organometallic (organo-transition metal) pharmaceuticals. Appl Organomet Chem. 2005;19:1-10.

Amersi et al., Ex vivo exposure to carbon monoxide prevents hepatic ischemia/reperfusion injury through p38 MAP kinase pathway. Hepatology. Apr. 2002;35(4):815-23.

Andreadis et al., Oxidative and nitrosative events in asthma. Free Radic Biol Med. Aug. 1, 2003;35(3):213-25. Review. Abstract only.

Angelici et al., Carboxamido carbonyl complexes of manganese(I). Inorg Chim Acta. Mar. 1968;2:3-7. Abstract only.

Angelici, Preparation, characterization, and reactions of the cis-Dihalotetracarbonylmanganate(I)anions. Inorg Chem. Aug. 1964:3(8):1099-1102.

Aujard et al., Tridemethylisovelleral, a potent cytotoxic agent. Bioorg Med Chem. Nov. 15, 2005;13(22):6145-50. Epub Aug. 1, 2005. Abstract only.

Bagul et al., Carbon monoxide protects against ischemia-reperfusion injury in an experimental model of controlled nonheartbeating donor kidney. Transplantation. Feb. 27, 2008;85(4): 576-81.

Bani-Hani et al., Modulation of thrombin-induced neuroinflammation in BV-2 microglia by carbon monoxide-releasing molecule 3. J Pharmacol Exp Ther. Sep. 2006;318(3):1315-22. Epub Jun. 13, 2006.

Bannenberg et al., Therapeutic applications of the gaseous mediators carbon monoxide and hydrogen sulfide. Expert Opin Ther Pat. May 2009;19(5):663-82. Review.

Barkoudah et al., The permissive role of endothelial NO in CO-induced cerebrovascular dilation. Am J Physiol Heart Circ Physiol. Oct. 2004;287(4):H1459-65. Epub Jun. 10, 2004.

Bauerová et al., Role of reactive oxygen and nitrogen species in etiopathogenesis of rheumatoid arthritis. Gen Physiol Biophys. Oct. 1999;18 Spec No:15-20. Review. Abstract only.

Beal, Oxidatively modified proteins in aging and disease. Free Radic Biol Med. May 1, 2002;32(9):797-803. Review. Abstract only.

Beaty et al., An in vitro model for the in vivo mobilization of cadmium by chelating agents using 113Cd-NMR spectroscopy. Chem Res Toxicol. 1992;5:568-75. Abstract only.

Berman et al., Sensitization and catalysis of light-induced decarbonylation of aldehydes. J Am Chem Soc. 1963;85(24):4010-4013.

Boissiere et al., Exercise and vasorelaxing effects of CO-releasing molecules in hypertensive rats. Med Sci Sports Exerc. Apr. 2006;38(4):652-9.

Botros et al., Interaction between endogenously produced carbon monoxide and nitric oxide in regulation of renal afferent arterioles. Am J Physiol Heart Circ Physiol. Dec. 2006;291(6):H2772-8. Epub Jul. 14, 2006.

Brooks et al., The spoilage characteristics of ground beef packaged in high-oxygen and low-oxygen modified atmosphere packages. Proc. Reciprocal Meat Conference. University of Illinois at Urbana-Champaign. 2006.

Bundgaard et al., Pro-drugs as delivery systems. Pharm Int. 1981;2:136-40.

Bundgaard et al., Pro-drugs as drug delivery systems XX. Oxazolidines as potential pro-drug types for β-aminoalcohols, aldehydes or ketones. Intl J Pharm. Feb. 1982;10(2):165-75. Abstract only.

Burgmayer et al., Synthesis and structure of a 7-coordinate molybdenum carbonyl fluoride derivative—Et4n Mo(Co)2(S2cnet2)2f. Inorganic Chem. 1985;24:2224-30.

Campbell et al., Molecular targets in immune-mediated diseases: the case of tumour necrosis factor and rheumatoid arthritis. Immunol Cell Biol. Oct. 2003;81(5):354-66.

Cepinskas et al., Carbon monoxide liberated from carbon monoxide-releasing molecule CORM-2 attenuates inflammation in the liver of septic mice. Am J Physiol Gastrointest Liver Physiol, Jan. 2008; 294:G184-G191.

Chakravortty et al., Inducible nitric oxide synthase and control of intracellular bacterial pathogens. Microbes Infect. Jun. 2003;5(7):621-7. Review. Abstract only.

Chatterjee, Water-soluble carbon monoxide-releasing molecules: helping to elucidate the vascular activity of the 'silent killer'. Br J Pharmacol. Jun. 2004;142(3):391-3. Epub May 17, 2004.

Chlopicki et al., Carbon monoxide released by CORM-3 inhibits human platelets by a mechanism independent of soluble guanylate cyclase. Cardiovasc Res. Jul 15, 2006;71(2):393-401. Epub Mar. 22, 2006

Cihonski et al., Crown ethers in inorganic chemistry—preparation and characterization of group 6 pentacarbonyl hydroxides and fluorides. Inorganic Chem. 1975;14:1717-20.

Clark et al., Measuring left ventricular function in the normal, infarcted and CORM-3-preconditioned mouse heart using complex admittance-derived pressure volume loops. J Pharmacol Methods. Mar.-Apr. 2009;59(2):94-9.

Coceani, Carbon monoxide in vasoregulation: the promise and the challenge. Circ Res. Jun. 23, 2000;86(12):1184-6. Review.

Cohen et al., Dithiobenzoatote tracarbonylmanganese(I). Inorg Chem. 1964;3(11):1641-42.

Conant et al., The action of the rignard reagent on highly branched carbonyl compounds. J Am Chem Soc. 1929;51(4):1246-55.

Cotton et al., Dimethyl- and diethyldithiocarbamate complexes of some metal carbonyl compounds. Inorg Chem. Jun. 2, 1964;3:1398-1402.

Cotton et al., X-ray molecular structures of Mn(CO)5(O2CCF3) and Mn(CO)3(C5H5N)2(O2CCF3). Inorg Chem. 1981;20(4):1287-91.

De Backer et al., Role of the soluble guanylyl cyclase alpha1/alpha2 subunits in the relaxant effect of CO and CORM-2 in murine gastric fundus. Naunyn Schmiedebergs Arch Pharmacol. Nov. 2008;378(5):493-502. Epub Jun. 18, 2008.

De Backer et al., Water-soluble CO-releasing molecules reduce the development of postoperative ileus via modulation of MAPK/HO-1 signalling and reduction of oxidative stress. Gut. Mar. 2009;58(3):347-56. Epob Nov. 20, 2008.

De Filippo et al., Inductive effect in dithiocarbanate decomposition mechanism. J Org Chem. 1973;38(3):560-3.

Desmard et al., A carbon monoxide-releasing molecule (CORM-3) exerts bactericidal activity against *Pseudomonas aeruginosa* and improves survival in an animal model of bacteraemia. FASEB J. Apr. 2009;23(4):1023-31. Epub Dec. 18, 2008.

Desmard et al., Carbon monoxide reduces the expression and activity of matrix metalloproteinases 1 and 2 in alveolar epithelial cells. Cell Mol Biol (Noisy-le-grand). Sep. 30, 2005;51(4):403-8.

Di Pascoli et al., Chronic CO levels have [corrected] a beneficial effect on vascular relaxation in diabetes. Biochem Biophys Res Commun. Feb. 17, 2006;340(3):935-43. Epub Dec. 27, 2005. Erratum in: Biochem Biophys Res Commun. Mar. 14, 2006;342(3):1003.

Douglas et al., Preparation of some group Vi fluorometal carbonyl derivatives. J Organometal Chem. 1974;65:665-9.

Drew et al., Synthesis, spectral properties, and reactions of manganese and rhenium pentacarbonyl phosphine and phosphite cation derivatives and related complexes. Inorg. Chem. 1975;14(7):1579-84.

Dröge et al., Free radicals in the physiological control of cell function. Physiol Rev. Jan. 2002;82(1):47-95. Review.

Duchëne et al., Cyclodextrins in targeting. Application to nanoparticles. Adv Drug Deliv Rev. Mar. 1, 1999;36(1):29-40.

Elliott et al., Nitric oxide: a regulator of mucosal defense and injury. J Gastroenterol. Dec. 1998;33(6):792-803. Review. Abstract only.

El-Sayed et al., Catalysis by crown ether complexes—part III effect of cation on the catalytic activity of crown ether—alkali metal halide complexes in the liquid phase oxidation of ethylbenzene. Egypt J Chem. 1979;22(1):23-8.

Fairlamb et al., Eta4-pyrone iron(0)carbonyl complexes as effective CO-releasing molecules (CO-RMs). Bioorg Med Chem Lett. Feb. 15, 2006;16(4):995-8. Epub Nov. 11, 2005.

Fang, Antimicrobial reactive oxygen and nitrogen species: concepts and controversies. Nat Rev Microbiol. Oct. 2004;2(10):620-32. Review. Abstract only.

Feldmann et al., Anti-TNF alpha therapy of rheumatoid arthritis: what have we learned? Annu Rev Immunol. 2001;19:163-96. Review.

Ferrándiz et al., Treatment with a CO-releasing molecule (CORM-3) reduces joint inflammation and erosion in murine collagen-induced arthritis. Ann Rheum Dis. Sep. 2008;67(9):1211-7. Epub Dec. 6, 2007.

Fischer et al., Methylpyridin-Chrom(0)-Tricarbonyl. Zeitschrift Fur Naturforschung Part-B-Chemie Biochemie Biophysik Biologie Und Verwandten Gebiete. 1959;14:736-7.

Fischer et al., Uber aromatenkomplexe von metallen .37. zur aromatenkomplexebildung des pyridins mit chromhexacarbonyl. Chemische berichte-recueil. 1960;93:1156-61. English abstract provided.

Fischer, Crystal structure of 1,4,7,10,13-pentaoxacylcopentadecane sodium bromide, C10H20BrNaO5. Zeitschrift fur kristallographie. 1996;2001:827-8.

Fiumana et al., Carbon monoxide mediates vasodilator effects of glutamate in isolated pressurized cerebral arterioles of newborn pigs. Am J Physiol Heart Circ Physiol. Apr. 2003;284(4): H1073-9.

Foresti et al., Reviewing the use of carbon monoxide-releasing molecules (CO-RMs) in biology: implications in endotoxin-mediated vascular dysfunction. Cell Mol Biol (Noisy-le-grand). Sep 30, 2005;51(4):409-23.

Foresti et al., Vasoactive properties of CORM-3, a novel water-soluble carbon monoxide-releasing molecule. Br J Pharmacol. Jun. 2004;142(3):453-60. Epub May 17, 2004.

Frangogiannis et al., The inflammatory response in myocardial infarction. Cardiovasc Res. Jan. 2002;53(1):31-47. Review.

Giboreau et al., Procedure for the preparation of pure dithiocarbamates. J Org Chem. 1994;59:1205-7.

Greener, Now you're signaling, with gas: gasotransmitters open a window on biology and drug development. The Scientist. 2004;18(17):20.

Guo et al., Administration of a CO-releasing molecule at the time of reperfusion reduces infarct size in vivo. Am J Physiol Heart Circ Physiol. May 2004;286(5):H1649-53. Epub Jan. 2, 2004.

Haag et al., Polymer therapeutics: concepts and applications. Angew Chem Int Ed Engl. Feb. 13, 2006;45(8):1198-215. Review. Abstract only.

Haddleton et al., [N-Alkyl-(2-pyridyl)methanimine]copper(I) complexes: characterisation and application as catalysts for atom-transfer polymerisation. Dec. 7, 1998;1998(11):1799-1806. Abstract only.

Haddleton et al., Atom transfer polymerization of methyl methacrylate mediated by alkylpyridylmethanimine type ligands, copper(I) bromide, and alkyl halides in hydrocarbon solution. Macromolecules. 1999;32(7):2110-19. Abstract only.

Hadjigogos, The role of free radicals in the pathogenesis of rheumatoid arthritis. Panminerva Med. Mar. 2003;45(1):7-13. Review. Abstract only.

Hall et al., DNA interaction with metal complexes and salts of substituted boranes and hydroborates in murine and human tumor cell lines. Anticancer Drugs. Aug. 1991;2(4):389-99.

Hall et al., The anti-inflammatory activity of metal complexes and salts of amine carboxyboranes. Appl Organomett Chem. 1994;8:473-80.

Hall et al., The hypolipidemic activity of metal complexes of amine carboxyboranes in rodents. Met Based Drugs. 1994;1(4):329-36.

Henricks et al., Reactive oxygen species as mediators in asthma. Pulm Pharmacol Ther. 2001;14(6):409-20. Review. Abstract only.

Hieber et al., Derivate des Mangancarbonyls mit schwefelorganischen Liganden. Chemische Berichte. 1966;99(7):2312-21. English abstract provided.

Hitchon et al., Oxidation in rheumatoid arthritis. Arthritis Res Ther. 2004;6(6):265-78. Epub Oct. 13, 2004. Review.

Hogg, Free radicals in disease. Semin Reprod Endocrinol. 1998;16(4):241-8. Review. Abstract only.

Holmuhamedov et al., Mitochondrial ATP-sensitive K+ channels modulate cardiac mitochondrial function. Am J Physiol. Nov. 1998;275(5 Pt 2):H1567-76.

Hosgood et al., Application of nitric oxide and carbon monoxide in a model of renal preservation. Br J Surg. Aug. 2008;95(8):1060-7.

Ignat'ev et al., Reactivity of perfluoroakyl halides towards nucleophiles. Russ J Electrochem. 1995;31(12):1235-9. Translated from Elektrokhimiya. 1995:31(12):1337-42.

Jander et al., Neutralisationenanaloge reaktionen in essigaureanhybrid. Zietschrift fur anorganische chemie. 1948;255:238-52. English abstract provided.

Jellum et al., Quantitative determination of biologically important thiols and disulfides by gas-liquid chromatography. Analyt Biochem. 1969;31:339-47. Abstract only.

Johansen et al., Spectrophotometric determination of the rates of hydrolysis of aldehyde-releasing pro-drugs in aqueous solution and plasma. Intl J Pharma. Dec. 1982;13(1):89-98. Abstract only.
Johnson et al., Metal carbonyls as pharmaceuticals? [Ru(CO)3C1(glycinate)], a CO-releasing molecule with an extensive aqueous solution chemistry. Dalton Trans. Apr. 21, 2007;(15):1500-8. Epub Mar. 8, 2007.
Józkowicz et al., Heme oxygenase and angiogenic activity of endothelial cells: stimulation by carbon monoxide and inhibition by tin protoporphyrin-IX. Antioxid Redox Signal. Apr. 2003;5(2):155-62.
Kharitonov et al., Basis of guanylate cyclase activation by carbon monoxide. Proc Natl Acad Sci U S A. Mar. 28, 1995;92(7):2568-71.
Kuiate et al., Composition of the essential oil from leaves and flowers of *Dichrocephala integrifolia* (L.) O. Kuntze Chev. From Cameroon. Flavour and Fragrance J. Nov./Dec. 1999;14(6):419-20. Abstract only.
Krueger et al., Potential of tumor necrosis factor inhibitors in psoriasis and psoriatic arthritis. Arch Dermatol. Feb. 2004;140(2):218-25. Review.
Lambert et al., O,O'-Diphenyldithiophosphatotetracarbonylmanganese(I) and related compounds. Inorg Chem. 1966;5(7):1287-9.
Lawton et al., Myocardial oxygen consumption in the rabbit heart after ischemia: hyperpolarized arrest with pinacidil versus depolarized hyperkalemic arrest. Circulation. Nov. 4, 1997;96(9 Suppl):II-247-52.
Ledger, Carbon monoxide-releasing metal carbonyls: a new class of pharmaceuticals? Drug Disc Today. 2003;8:1096.
Lee et al., Heme oxygenase-1 mediates the anti-inflammatory effect of interleukin-10 in mice. Nat Med. Mar. 2002;8(3):240-6.
Levrand et al., Controlled release of volatile aldehydes and ketones by reversible hydrazone formation—classical profragrances are getting dynamic. Chem. Commun. 2006;28:2965-7.
Li et al., Carbon monoxide protects PC12 cells from peroxynitrite-induced apoptotic death by preventing the depolarization of mitochondrial transmembrane potential. Biochem Biophys Res Commun. Apr. 14, 2006;342(3):984-90.
Loftsson et al., Cyclodextrins in topical drug formulations: theory and practice. Int J Pharm. Aug. 28, 2001;225(1-2):15-30. Review.
Lovell, Biologic agents for the treatment of juvenile rheumatoid arthritis: current status. Paediatr Drugs. 2004;6(3):137-46.
Mahmoud et al., Potential anticancer agents. XVI. Isolation of bicyclofarnesane sesquiterpenoids from Capsicodendron dinisii. J Nat Prod. May-Jun. 1980;43(3):365-71. Abstract only.
Martins et al., Induction of carbon monoxide in the donor reduces graft immunogenicity and chronic graft deterioration. Transplant Proc. Jan.-Feb. 2005;37(1):379-81.
Matsuda et al., Mediators of non-adrenergic non-cholinergic inhibitory neurotransmission in porcine jejunum. Neurogastroenterol Motil. Oct. 2004;16(5):605-12.
Mattes et al., Triply bridged thiobenzoato carbonyl manganates(I) and rhenates(I). The crystal and molecular structure of caesium tris(μ-thiobenzoatos(S))bis(tricarbonyl rhenate). J Organometall Chem. Sep. 25, 1979; 178(1):191-6.
McMillen et al., Hydrocarbon bond dissociation energies. Ann Rev Phys Chem. Oct. 1982;33:493-532.
Meder et al., Metallkomplexe mit biologisch wichtigen liganden, XLII [1] carbonylmetallkomplexe mit anionen von mehrfunktionellen alpha-aminosaeuren [Metal complexes with biologically important ligands), XLII [1] carbonyl metal complexes with anions of polyfunctional alpha-amino acids]. Zeitchrift fur Naturforschung;1986:1247-54. German language reference. English abstract provided.
Megias et al., The carbon monoxide-releasing molecule tricarbonyldichlororuthenium(II) dimer protects human osteoarthritic chondrocytes and cartilage from the catabolic actions of interleukin-1beta. J Pharmacol Exp Ther. Apr. 2008;325(1):56-61. Epub Jan. 14, 2008.
Miguel et al., Manganese(I) complexes with (tricyclohexylphosphonio)dithiocarboxylate as chelate and unidentate ligand. X-Ray crystal structure of fac[Mn(CO)3[S2CP(C6H11]3}2]C1O4oH2O. J Chem Soc, Dalton Trans. 1987;12:2875-80.
Mikuls et al., Benefit-risk assessment of infliximab in the treatment of rheumatoid arthritis. Drug Saf. 2003;26(1):23-32. Review. Abstract only.
Miller et al., The pharmacological activities of the metabolites of N-[(trimethylamineboryI)- carbonyl]-L-phenylalanine methyl ester. Met Based Drugs. 1996;3(5):219-26.
Moncada et al., The discovery of nitric oxide and its role in vascular biology. Br J Pharmacol. Jan. 2006;147 Suppl 1:S193-201.
Moore et al., Brief inhalation of low-dose carbon monoxide protects rodents and swine from postoperative ileus. Crit Care Med. Jun. 2005;33(6):1317-26.
Morse et al, Suppression of inflammatory cytokine production by carbon monoxide involves the JNK pathway and AP-1. J Biol Chem. Sep. 26, 2003;278(39):36993-8. Epub Jul. 11, 2003.
Motterlini et al., CORM-A1: a new pharmacologically active carbon monoxide-releasing molecule. FASEB J. Feb. 2005;19(2):284-286. Epub Nov. 19, 2004.
Motterlini et al., Functional and metabolic effects of propionyl-L-carnitine in the isolated perfused hypertrophied rat heart. Mol Cell Biochem. Oct. 21, 1992;116(1-2):139-45.
Motterlini et al., Therapeutic applications of carbon monoxide-releasing molecules. Expert Opin Investig Drugs. Nov. 2005;14(11):1305-18. Review.
Motterlini, Vasoactive properties of carbon monoxide-releasing molecules. Biomed Pharmacother. 2002;56(7):349-50.
Moya et al., Metal carbonyl complexes containing heterocyclic nitrogen ligands: Part IX. MnBr(CO)3(3,3?-R-2,2?-biquinoline) compounds. Polyhedron. Mar. 1, 2002; 21(4):439-44. Abstract only.
Mungrue et al., From molecules to mammals: what's NOS got to do wth it? Acta Physiol Scand. Oct. 2003;179(2):123-35. Review. Abstract only.
Musameh et al., Improved myocardial function after cold storage with preservation solution supplemented with a carbon monoxide-releasing molecule (CORM-3). J Heart Lung Transplant. Nov. 2007;26(11):1192-8.
Musameh et al., Positive inotropic effects of carbon monoxide-releasing molecules (CO-RMs) in the isolated perfused rat heart. Br J Pharmacol. Dec. 2006;149(8):1104-12. Epub Oct. 23, 2006.
Nakao et al., Carbon monoxide inhalation protects rat intestinal grafts from ischemia/reperfusion injury. Am J Pathol. Oct. 2003;163(4):1587-98.
Nakao et al., Protective effect of carbon monoxide in transplantation. J Cell Mol Med. Jul.-Sep. 2006;10(3):650-71. Review.
Nathan, Points of control in inflammation. Nature. Dec. 19-26, 2002;420(6917):846-52. Review.
Ndisang et al., Modulation of the immunological response of guinea pig mast cells by carbon monoxide. Immunopharmacology. Jun. 1999;43(1):65-73.
Neto et al., Protection of transplant-induced renal ischemia-reperfusion injury with carbon monoxide. Am J Physiol Renal Physiol. Nov. 2004;287(5):F979-89. Epub Aug. 3, 2004.
Nitschke et al., Properties of (trifluoromethanesulfonato)pentacarbonylmanganese(I) and—rhenium(I). Reactions in superacid solvents. Inorg Chem. 1985;24(13):1972-8.
Nobre et al., Antimicrobial action of carbon monoxide-releasing compounds. Antimicrob Agents Chemother. Dec. 2007;51(12);4303-7. Epub Oct. 8, 2007.
Nudelman et al., Prodrugs of butyric acid. Novel derivatives possessing increased aqueous solubility and potential for treating cancer and blood diseases. Eur J Med Chem. Jan. 2001;36(1):63-74. Abstract only.
Nudelman et al., The role of Intracellularly released formaldehyde and butyric acid in the anticancer activity of acyloxyalkyl esters. J. Med. Chem.. Jan. 22, 2005;48(4):1042-54. Abstract only.
Nydegger et al., New concepts in organ preservation. Transpl Immunol. May 2002;9(2-4):215-25.
O'Brien et al., Aldehyde sources, metabolism, molecular toxicity mechanisms, and possible effects on human health. Crit Rev Toxicol. Aug. 2005;35(7):609-62. Review.

Otterbein et al., Carbon monoxide suppresses arteriosclerotic lesions associated with chronic graft rejection and with balloon injury. Nat Med. Feb. 2003;9(2):183-90. Epub Jan. 21, 2003.

Otterbein et al., Heme oxygenase-1: unleashing the protective properties of heme. Trends Immunol. Aug. 2003;24(8):449-55. Review.

Ozawa et al., Leydig cell-derived heme oxygenase-1 regulates apoptosis of premeiotic germ cells in response to stress. J Clin Invest. Feb. 2002;109(4):457-67.

Pae et al., Carbon monoxide produced by heme oxygenase-1 suppresses T cell proliferation via inhibition of IL-2 production. J Immunol. Apr. 15, 2004;172(8):4744-51.

Paintner et al., Synthesis and antimicrobial activity of tetrodecamycin partial structures. Bioorg Med Chem. Jul. 3, 2003;11(13):2823-33. Abstract only.

Pankey et al., Clinical relevance of bacteriostatic versus bactericidal mechanisms of action in the treatment of Gram-positive bacterial infections. Clin Infect Dis. Mar. 15, 2004;38(6):864-70. Epub Mar. 1, 2004. Review.

Patel et al., Preparation of (η5-cyclopentadienyl) and (η5-Methylcyclopentadienyl)Fe(CO)2Me cyclodextrin inclusion compounds and their subsequent ligand substitution reactions. Attempts at cyclodextrin mediated enantioselective ligand substitution. J Organometal Chem. 1997;547:103-112.

Peloso et al., Expanding the armamentarium for the spondyloarthropathies. Arthritis Res Ther. 2004;6 Suppl 2:S36-43. Epub Jun. 21, 2004.

Piantadosi, Biological chemistry of carbon monoxide. Antioxid Redox Signal. Apr. 2002;4(2):259-70. Review.

Quick et al., Pentacarbonylmanganese halides. In Inorganic Syntheses, vol. 19. Duward F. Shriver., Ed. Inorganic Syntheses, Inc. 1979.

Rattan et al., Mechanism of internal anal sphincter relaxation by CORM-1, authentic CO, and NANC nerve stimulation. Am J Physiol Gastrointest Liver Physiol. Sep. 2004;287(3):G605-11.

Rehder et al., 55Mn NMR characteristics of carbonylmanganese complexes with hetero-substituted dithioformato-, thioformamido- and thioformamide ligands (1). Inorg Chim Acta. 1983;73:243-7. Abstract only.

Reimann et al., Reactions of metal carbonyls. Part III. Steric and stereochemical limitations of higher substitution of manganese carbonyl bromide. J Chem Soc Dalton Trans. 1973;841-6. Abstract only.

Rodella et al., Carbon monoxide and biliverdin prevent endothelial cell sloughing in rats with type I diabetes. Free Radic Biol Med. Jun. 15, 2006;40(12):2198-205. Epub Mar. 20, 2006.

Ryan et al., Renal vascular responses to CORM-A1 in the mouse. Pharmacol Res. Jul. 2006;54(1):24-29. Epub Mar. 9, 2006.

Ryter et al., Carbon monoxide in biology and medicine. Bioessays. Mar. 2004;26(3):270-80.

Ryter et al., Carbon monoxide: to boldly go where NO has gone before. Sci STKE. Apr. 20, 2004;(230):RE6. Review.

Ryter et al., Heme oxygenase/carbon monoxide signaling pathways: regulation and functional significance. Mol Cell Biochem. May-Jun. 2002;234-235(1-2):249-63. Review.

Ryter et al., Heme oxygenase-1/carbon monoxide: from basic science to therapeutic applications. Physiol Rev. Apr. 2006;86(2):583-650. Review.

Sandborn, Strategies for targeting tumour necrosis factor in IBD.Best Pract Res Clin Gastroenterol. Feb. 2003;17(1):105-17. Review.

Sandouka et al., Carbon monoxide-releasing molecules (CO-RMs) modulate respiration in isolated mitochondria. Cell Mol Biol (Noisy-le-grand). Sep. 30, 2005;51(4):425-32.

Sandouka et al., Treatment with CO-RMs during cold storage improves renal function at reperfusion. Kidney Int. Jan. 2006;69(2):239-47.

Sarady et al., Carbon monoxide protection against endotoxic shock involves reciprocal effects on iNOS in the lung and liver. FASEB J. May 2004;18(7):854-6. Epub Mar. 4, 2004.

Sawle et al., Carbon monoxide-releasing molecules (CO-RMs) attenuate the inflammatory response elicited by lipopolysaccharide in RAW264.7 murine macrophages. Br J Pharmacol. Jul. 2005;145(6):800-10.

Sawle et al., Homocysteine attenuates endothelial haem oxygenase-1 induction by nitric oxide (NO) and hypoxia. FEBS Lett. Nov. 23, 2001;508(3):403-6.

Schmidt et al., Manganese(I) and rhenium(I) pentacarbonyl(Trifluoromethanesulfatonato) complexes. In Inorganic Syntheses, Ed. Herbert D. Kaesz. Inorganic Syntheses, Inc. 1989.

Shapiro, Carbonyl-trapping therapeutic strategies. Am J Ther. Sep. 1998;5(5):323-53. Review.

Shiohira et al., Protective effect of carbon monoxide donor compounds in endotoxin-induced acute renal failure. Am J Nephrol. 2007;27(5):441-6. Epub Jul. 12, 2007.

Song et al., Carbon monoxide inhibits T lymphocyte proliferation via caspase-dependent pathway. J Immunol. Jan. 15, 2004;172(2):1220-6.

Spector, Review: Oxidative stress and disease. J Ocul Pharmacol Ther. Apr. 2000;16(2):193-201. Review. Abstract only.

Srisook et al., CO from enhanced HO activity or from CORM-2 inhibits both O2- and NO production and downregulates HO-1 expression in LPS-stimulated macrophages. Biochem Pharmacol. Jan. 12, 2006;71(3):307-18. Epub Dec. 2, 2005.

Srisook et al., Role of NO in enhancing the expression of HO-1 in LPS-stimulated macrophages. Methods Enzymoi 2005;396:368-77.

Staal et al., The syntheses and coordination properties of M(CO)3X(DAB) (M= Mn, Re; X= Cl, Br, I; DAB= 1,4-diazabutadiene). J Organometal Chem. May 1, 1979:170( 2):235-45. Abstract only.

Stagni et al., A water-soluble carbon monoxide-releasing molecule (CORM-3) lowers intraocular pressure in rabbits. Br J Ophthalmol. Feb. 2009;93(2):254-7. Epub Oct. 31, 2008.

Stanford et al., Carbon monoxide inhibits endothelin-1 release by human pulmonary artery smooth muscle cells. Eur J Pharmacol. Feb. 23, 2004;486(3):349-52.

Stanford et al., Heme oxygenase is expressed in human pulmonary artery smooth muscle where carbon monoxide has an anti-proliferative role. Eur J Pharmacol. Jul. 25, 2003;473(2-3):135-41.

Stec et al., Heme oxygenase-1 induction does not improve vascular relaxation in angiotensin II hypertensive mice. Am J Hypertens. Feb. 2008;21(2) 189-93. Epub Jan. 3, 2008.

Stein et al., Administration of a CO-releasing molecule induces late preconditioning against myocardial infarction. J Mol Cell Cardiol. Jan. 2005;38(1):127-34. Epub Dec. 8, 2004.

Stone et al., Synergistic activation of soluble guanylate cyclase by YC-1 and carbon monoxide: implications for the role of cleavage of the iron-histidine bond during activation by nitric oxide. Chem Biol. May 1998;5(5):255-61.

Sun et al., Attenuation of leukocytes sequestration by carbon monoxide-releasing molecules: liberated carbon monoxide in the liver of thermally injured mice. J Burn Care Res. Jan.-Feb. 2007;28(1):173-81.

Sun et al., CO-releasing molecules (CORM-2)-liberated CO attenuates leukocytes infiltration in the renal tissue of thermally injured mice. Int J Biol Sci. Jun. 16, 2008;4(3):176-83.

Sun et al., Preconditioning of carbon monoxide releasing molecule-derived CO attenuates LPS-induced activation of HUVEC. Int J Biol Sci. Aug. 22, 2008;4(5):270-8.

Sun et al., Role of CO-releasing molecules liberated CO in attenuating leukocytes sequestration and inflammatory responses in the lung of thermally injured mice. J Surg Res. May 1, 2007;139(1):128-35. Epub Feb. 9, 2007.

Suzuki et al., Activated platelets in ulcerative colitis enhance the production of reactive oxygen species by polymorphonuclear leukocytes. Scand J Gastroenterol. Dec. 2001;36(12):1301-6. Abstract only.

Szallasi et al., Dialdehyde sesquiterpenes and other terpenoids as vanilloids. Eur J Pharmacol. Aug. 28, 1998;356(1):81-9. Abstract only.

Taillé et al., Mitochondrial respiratory chain and NAD(P)H oxidase are targets for the antiproliferative effect of carbon monoxide in human airway smooth muscle. J Biol Chem. Jul. 8, 2005;280(27):25350-60. Epub Apr. 29, 2005.

Tayem et al., Protection against cisplatin-induced nephrotoxicity by a carbon monoxide-releasing molecule. Am J Physiol Renal Physiol. Apr. 2006,290(4):F789-94. Epub Nov. 15, 2005.

Tilg et al., Antitumour necrosis factor therapy in Crohn's disease. Expert Opin Biol Ther. Oct. 2002;2(7):715-21. Review. Abstract only.

Treichel et al., Synthesis and reactivity of bridging thiolato-manganese carbonyl complexes, Et4N[Mn2(μ-SR)3(CO)6]. J Organometall Chem. Sep. 10, 1985;292(3):385-93.

Urwyler et al., Positive allosteric modulation of native and recombinant gamma-aminobutyric acid(B) receptors by 2,6-Di-tert-butyl-4-(3-hydroxy-2,2-dimethyl-propyl)-phenol (CGP7930) and its aldehyde analog CGP13501. Mol Pharmacol. Nov. 2001;60(5):963-71.

Van Staveren et al., Spectroscopic Properties, Electrochemistry, and Reactivity of MoO, MoI, and MoII Complexes with the [Mo(bpa)(CO)3] Unit [bpa= bis(2-picolyl)amine] and Their Application for the Labelling of Peptides. Eur J Inorg Chem. 2002;6:1518-29.

Vannacci et al., Evaluation of the effects of a novel carbon monoxide releasing molecule (CORM-3) in an in vitro model of cardiovascular inflammation. 1. Histamine in allergy, inflammation, tissue growth and repair. Inflamm Res. Apr. 2006;55 Suppl 1:S05-6.

Vannacci et al., The effect of a carbon monoxide-releasing molecule on the immunological activation of guinea-pig mast cells and human basophils. Inflamm Res. 2004;53 Suppl 53:S09-10.

Varadi et al., Beneficial effects of carbon monoxide-releasing molecules on post-ischemic myocardial recovery. Life Sci. Apr. 3, 2007;80(17):1619-26. Epub Feb. 2, 2007.

Vera et al., Protective effect of carbon monoxide-releasing compounds in ischemia-induced acute renal failure. J Am Soc Nephrol. Apr. 2005;16(4):950-8. Epub Feb. 23, 2005.

Verona et al., Regioselectivity in the nucleophilic functionalization of xanthene complexes of Mn(CO)3. J Organelle Chem. Nov. 1, 1996;524(1-2)71-80.

Volti et al., Carbon monoxide signaling in promoting angiogenesis in human microvessel endothelial cells. Antiox Redox Signal. May 2005;7(5-6):704-10.

Vreman et al., Determination of carbon monoxide (CO) in rodent tissue: effect of heme administration and environmental CO exposure. Anal Biochem. Jun. 15, 2005;341(2):280-9. Abstract only.

Wang et al., Preconditioning limits mitochondrial Ca(2+) during ischemia in rat hearts: role of K(ATP) channels. Am J Physiol Heart Circ Physiol. May 2001;280(5):H2321-8.

Wang et al., The chemical modification of KCa channels by carbon monoxide in vascular smooth muscle cells. J Biol Chem. Mar. 28, 1997;272(13)8222-6.

Weigel et al., Inhibition of DNA replication in *Escherichia coli* by cyanide and carbon monoxide. J Biol Chem. Nov. 10, 1975;250(21):8536-42.

Wu et al., Carbon monoxide: endogenous production, physiological functions, and pharmacological applications. Pharmacol Rev. Dec. 2005;57(4):585-630. Review.

Xi et al., Carbon monoxide activates KCa channels in newborn arteriole smooth muscle cells by increasing apparent Ca2+ sensitivity of alpha-subunits. Am J Physiol Heart Circ Physiol. Feb. 2004;286(2):H610-8. Epub Oct. 16, 2003.

Xu et al., A facile method for synthesis of (R)-(-)- and (S)-(+)-homocitric acid lactones and related α-hydroxy dicarboxylic acids from d- or l-malic acid. Tetrahedron Lett. May 30, 2005;46(22):3815-18. Abstract only.

Zhang et al., Carbon monoxide inhibition of apoptosis during ischemia-reperfusion lung injury is dependent on the p38 mitogen-activated protein kinase pathway and involves caspase 3. J Biol Chem. Jan. 10, 2003;278(2)1248-58. Epub Oct. 23, 2002.

Zimmerman at al., Cerebroprotective effects of the CO-releasing molecule CORM-A1 against seizure-induced neonatal vascular injury. Am J Physiol Heart Circ Physiol. Oct. 2007;293:H2501-H2507.

Zuckerbraun et al., Carbon monoxide protects against the development of experimental necrotizing enterocolitis. Am J Physiol Gastrointest Liver Physiol. Sep. 2005;289(3):G607-13. Epub May 12, 2005.

Zuckerbraun et al., Carbon monoxide reverses established pulmonary hypertension. J Exp Med. Sep. 4, 2006;203(9):2109-19. Epub Aug. 14, 2006.

Abe et al., The effects of prostacyclin analog OP-41483 on normothermic liver ischemia and reperfusion injury in rats. Prostaglandins Leukot Essent Fatty Acids. Jun. 1993;48(6):417-22.

Burleson et al., The effect of dyes used to evaluate the in situ, ex-vivo, and perfused kidney. Invest Urol. Nov. 1981;19(3):165-8. Abstract only. Accession No. PREV198273058212.

Duckers et al., Heme oxygenase-1 protects against vascular constriction and proliferation. Nat Med. Jun. 2001;7(6):693-8.

Kubic et al., Metabolism of dihalomethanes to carbon monoxide. I. In vivo studies. Drug Metab Dispos. Jan.-Feb. 1974;2(1):53-7. Abstract only.

Loganson et al., Metal carbonyl complexes with ligands of biological origin. Russ Chem Rev. 1985;54(3):277-92.

Morita et al., Endothelial cell expression of vasoconstrictors and growth factors is regulated by smooth muscle cell-derived carbon monoxide. J Clin Invest. Dec. 1995;96(6):2676-82.

Siow et al., Heme oxygenase-carbon monoxide signalling pathway in atherosclerosis: anti-atherogenic actions of bilirubin and carbon monoxide? Cardiovasc Res. Feb. 1999;41(2):385-94.

Togane et al., Protective roles of endogenous carbon monoxide development elicited by arterial injury. Am J Physiol Heart Circ Physiol. Feb. 2000;278(2):H623-32.

* cited by examiner

Tricarbonyldichloro ruthenium(II) dimer
[Ru (CO)$_3$(Cl)$_2$]$_2$

| Compound | Structure | MW | CO Release (20 µmoles) | | | | CO Release (40 µmoles) | | | | NOTES |
|---|---|---|---|---|---|---|---|---|---|---|---|
| | | | 0 | 10 | 20 | 30 | 0 | 10 | 20 | 30 | |
| CO-RM-1 | [structure] | 512 | 12.0 ±3.0 | 16.3 ±4.0 | 18.1 ±4.3 | 18.5 ±4.8 | 28.5 ±0.4 | 32.0 ±0.2 | 34.5 ±0.5 | 35.6 ±0.4 | Soluble in DMSO |
| CO-RM-1a | [structure] | 384 | 7.2 ±0.6 | 8.6 ±0.3 | 8.0 ±0.4 | 7.5 ±0.4 | 16.9 ±0.6 | 18.4 ±0.3 | 17.3 ±0.3 | 16.7 ±0.2 | Soluble in DMSO |
| Negative control | [structure] | 484 | N.D. | N.D. | N.D. | N.D. | N.D. | N.D. | N.D. | N.D. | Soluble in $H_2O$ |
| CO-RM-1b | [structure] | 334 | 6.4 ±1.2 | 7.3 ±0.6 | 8.2 ±0.1 | 8.7 ±0.3 | 11.7 ±0.8 | 13.7 ±0.9 | 14.0 ±1.1 | 14.4 ±0.6 | Soluble in DMSO |
| CO-RM-10 | $[Ru(CO)_2Cl_2]_n$ | (228) | 2.6 ±0.6 | 9.8 ±0.3 | 12.7 ±0.1 | 13.8 ±0.9 | 8.6 ±0.7 | 21.0 ±1.1 | 24.4 ±1.0 | 26.3 ±1.2 | Soluble in DMSO |

Fig. 9(a)

| | | | | | | | | | | |
|---|---|---|---|---|---|---|---|---|---|---|
| CO-RM-11<br>Ligand: THF | 328 | 5.6<br>±0.6 | 5.9<br>±0.6 | 6.2<br>±1.1 | 6.2<br>±1.2 | 10.9<br>±0.2 | 12.3<br>±0.4 | 13.3<br>±0.4 | 13.7<br>±0.2 | Soluble in DMSO |
| CO-RM-16<br>Ligand: Cytidine | 742 | N.D. | 1.4<br>±0.4 | 2.1<br>±0.1 | 2.8<br>±0.4 | 0.8<br>±0.4 | 5.5<br>±0.4 | 8.4<br>±0.8 | 9.8<br>±0.9 | Soluble in $H_2O$ |
| CO-RM-17<br>Ligand: Guanosine | 539 | 5.9<br>±0.1 | 8.2<br>±0.4 | 8.5<br>±0.3 | 8.6<br>±0.4 | 11.5<br>±0.4 | 15.0<br>±0.4 | 15.6<br>±0.4 | 16.2<br>±0.3 | Soluble in $H_2O$ |

Fig. 9(b)

| | | | | | | | | | |
|---|---|---|---|---|---|---|---|---|---|
| CO-RM-18<br>Ligand:<br>Guanosine | 822 | 10.1<br>±0.9 | 14.3<br>±0.4 | 14.1<br>±0.5 | 13.5<br>±0.4 | 25.4<br>±1.0 | 29.5<br>±1.5 | 29.5<br>±1.4 | 28.7<br>±1.3 | Soluble in<br>$H_2O$ |
| CO-RM-22<br>Ligand:<br>Guanine | 407 | 0.1<br>±0.1 | 0.8<br>±0.3 | 1.0<br>±0.3 | 2.3<br>±0.1 | 0.7<br>±0.1 | 1.9<br>±0.1 | 2.3<br>±0.1 | 2.4<br>±0.1 | Soluble in<br>$H_2O$<br>PPT |
| CO-RM-23<br>Ligand:<br>Guanine | 558 | 1.2<br>±0.1 | 1.3<br>±0.2 | 1.3<br>±0.1 | 1.0<br>±0.2 | 2.7<br>±0.3 | 2.7<br>±0.3 | 2.7<br>±0.4 | 2.3<br>±0.2 | Soluble in<br>$H_2O$<br>PPT |
| CO-RM-26<br>Ligand:<br>Cysteine | 340.5 | 0.6<br>±0.1 | 1.9<br>±0.1 | 2.3<br>±0.2 | 2.4<br>±0.2 | 1.9<br>±0.2 | 3.7<br>±0.1 | 5.1<br>±0.1 | 5.2<br>±0.1 | Soluble in<br>$H_2O$ |

Fig. 9(c)

| | | | | | | | | | | |
|---|---|---|---|---|---|---|---|---|---|---|
| CO-RM-29<br>Ligand:<br>Triacetyle-<br>guanosine | [structure] | 665 | 1.4<br>±0.7 | 4.5<br>±0.1 | 5.0<br>±0.1 | 3.2<br>±0.1 | 8.3<br>±0.6 | 11.7<br>±0.3 | 12.4<br>±0.1 | 10.6<br>±0.4 | Soluble in<br>$H_2O$ |
| CO-RM-3<br>Ligand:<br>Glycine | [structure] | 294.5 | 14.2<br>±0.6 | 17.8<br>±0.7 | 14.3<br>±0.7 | 12.9<br>±0.7 | 25.2<br>±1.5 | 24.4<br>±1.0 | 23.8<br>±0.6 | 23.2<br>±0.3 | Soluble in<br>$H_2O$ |
| CO-RM-38<br>Ligand:<br>Isoleucine | [structure] | 350.5 | 3.2<br>±0.2 | 4.4<br>±0.1 | 4.0<br>±0.2 | 3.0<br>±1.7 | 7.6<br>±1.3 | 8.3<br>±1.2 | 7.5<br>±1.1 | 7.3<br>±1.1 | Soluble in<br>$H_2O$ |
| CO-RM-39<br>Ligand:<br>Serine | [structure] | 324.5 | 11.0<br>±.03 | 12.8<br>±.09 | 11.4<br>±1.1 | 10.8<br>±.07 | 24.2<br>±1.5 | 24.6<br>±1.4 | 22.0<br>±1.0 | 21.9<br>±1.2 | Soluble in<br>$H_2O$ |
| CO-RM-40<br>Ligand:<br>Alanine | [structure] | 308.5 | 9.1<br>±1.1 | 11.9<br>±0.4 | 11.1<br>±.03 | 11.0<br>±0.2 | 20.2<br>±.06 | 21.3<br>±.09 | 19.9<br>±.09 | 19.6<br>±.09 | Soluble in<br>$H_2O$ |

Fig. 9(d)

| | | | | | | | | | | |
|---|---|---|---|---|---|---|---|---|---|---|
| CO-RM-42<br>Ligand:<br>Glutamine | [structure] | 365.5 | 8.9<br>±0.4 | 11.1<br>±0.4 | 12.1<br>±1.4 | 10.1<br>±0.3 | 21.4<br>±2.1 | 21.8<br>±2.2 | 20.6<br>±2.0 | 20.0<br>±1.8 | Soluble in H₂O |
| CO-RM-43<br>Ligand:<br>Arginine | [structure] | 393.5 | 9.4<br>±1.4 | 11.9<br>±0.5 | 12.3<br>±0.7 | 11.0<br>±0.3 | 18.3<br>±.03 | 20.0<br>±0.6 | 19.0<br>±1.2 | 17.8<br>±1.3 | Soluble in H₂O |
| CO-RM-46<br>Ligand:<br>Lysine | [structure] | 365.5 | 6.0<br>±0.4 | 7.5<br>±0.8 | 7.2<br>±1.2 | 6.4<br>±0.8 | 12.6<br>±0.9 | 13.4<br>±1.2 | 13.2<br>±1.1 | 11.9<br>±1.0 | Soluble in H₂O |
| CO-RM-67<br>Ligand:<br>L-valine | [structure] | 336.5 | 11.1<br>±2.9 | 18.2<br>±1.7 | 17.6<br>±1.6 | 17.0<br>±1.6 | 29.3<br>±1.5 | 34.6<br>±2.2 | 33.7<br>±2.2 | 32.8<br>±2.2 | Soluble in H₂O |
| CO-RM-70 | [structure] | 240 | 0.5<br>±0.2 | 0.9<br>±0.1 | 2.2<br>±0.2 | 2.7<br>±0.3 | 0.9<br>±0.1 | 2.0<br>±0.2 | 4.9<br>±0.2 | 6.3<br>±0.3 | Soluble in DMSO PPT |
| CO-RM-71 | [structure] | 350 | 1.5<br>±0.2 | 2.3<br>±0.3 | 3.1<br>±0.4 | 3.7<br>±0.4 | 3.4<br>±0.1 | 5.4<br>±0.3 | 6.9<br>±0.3 | 7.6<br>±0.4 | Soluble in DMSO PPT |

Fig. 9(e)

| | | | | | | | | | | |
|---|---|---|---|---|---|---|---|---|---|---|
| CO-RM-74 Ligand: L-Threonine |  | 338.5 | 15.7 ±1.2 | 17.5 ±2.0 | 16.5 ±2.3 | 14.8 ±2.2 | 33.3 ±0.2 | 33.4 ±0.1 | 32.7 ±0.2 | 31.4 ±0.1 | Soluble in $H_2O$ |
| CO-RM-97 |  | 316 | 2.8 ±0.6 | 7.0 ±0.7 | 7.2 ±0.9 | 6.6 ±0.9 | 7.1 ±0.5 | 14.3 ±0.7 | 14.7 ±0.8 | 13.6 ±0.7 | Soluble in $H_2O$ |
| CO-RM-99 |  | 317 | 4.6 ±0.6 | 8.1 ±0.2 | 7.3 ±0.3 | 5.5 ±0.3 | 11.5 ±0.2 | 16.6 ±0.2 | 16.0 ±0.9 | 14.0 ±0.2 | Soluble in $H_2O$ |
| CO-RM-H Ligand: L-proline |  | 335 | 1.4 ±0.3 | 4.7 ±0.6 | 6.2 ±0.8 | 6.3 ±0.7 | 4.2 ±0.4 | 9.9 ±0.2 | 12.5 ±0.1 | 13.0 ±0.1 | Soluble in $H_2O$ |

THERAPEUTIC DELIVERY OF CARBON MONOXIDE

This is a divisional of Ser. No. 10/143,824, filed May 14, 2002 now U.S. Pat. No. 7,045,140 which claims benefit of GB 0111872.8, filed 15 May 2001, the entire contents of each of which is incorporated herein by reference.

FIELD OF THE INVENTION

The present invention relates to pharmaceutical compositions and compounds for the therapeutic delivery of carbon monoxide to humans and other mammals. Another use of the compositions and compounds is in organ perfusion.

BACKGROUND OF THE INVENTION

Carbon monoxide (CO) is, by common definition, a colorless, odorless, tasteless, non-corrosive gas of about the same density as that of air and is the most commonly encountered and pervasive poison in our environment, it is generally produced by the incomplete combustion of fossil fuels such as natural gas, propane, coal, gasoline end wood. In the atmosphere, the average global levels are estimated to be 0.19 parts per million (p.p.m.), 90% of which comes from natural sources including ocean micro-organism production, and 10% or which is generated by human activity. Thus, inhalation of even small quantities of CO is inevitable for living organisms.

Depending on the extent and time of exposure, CO is capable of producing a myriad of debilitating and harmful residual effects to the organism (1). The most immediate of these effects, and perhaps the most notorious one, is binding to hemoglobin in the blood stream, which rapidly decreases the oxygen transport capability of the cardiovascular system. Paradoxically, more than half a century ago it was found that CO is constantly formed in human in small quantities (2), and that under certain pathophysiological conditions this endogenous production of CO may be considerably increased (3-5). The discovery that hemoglobin, a heme-dependent protein, is required as substrate for the production of CO in vivo (6, 7) and the identification of the enzyme heme oxygenase as the crucial pathway for the generation of this gaseous molecule in mammals (8) set the basis for the early investigation of an unexpected and still unrecognized role of CO in the vasculature (9). The succeeding cloning (10) and characterization of constitutive (HO-2) and inducible (HO-1) isoforms of heme oxygenase (11-13) as well as studies on the kinetics and tissue distribution of these enzymes (14) started to reveal a major importance of this pathway in the physiological degradation of heme. That is, the end products of heme degradation (CO, biliverdin and bilirubin) might possess, after all, crucial biological activities (15-17).

With regard to the cardiovascular system, the recognition that CO possesses vasodilatory properties (18-20) is, perhaps, the most significant evidence in favor of a pharmacological function of CO. Although the molecular mechanisms and the chemical modifications that are required to transduce the signals mediated by CO into a specific biological effect need to be fully elucidated, convincing scientific reports have recently highlighted the signaling properties of endogenously generated CO (21-24).

Experimental studies on the physiological effects of nitric oxide (NO) have been facilitated by the development of a wide variety of organic compounds that spontaneously release NO and can be easily acquired to reproduce a physiological or pathophysiological function of NO. There is now abundant literature on the different types of NO donors and NO-releasing agents that, depending on their stability and half-life, can be used in disparate in vitro and in vivo models to simulate the biological activity of this important signaling molecule (25, 26). In clinical practice, compounds that deliver NO into the circulation such as sodium nitroprusside and glyceryl trinitrate are used to lower blood pressure and treat certain cardiovascular diseases (27). Drugs containing a functional NO group that can selectively target an organ or tissue are currently being developed or are under clinical trials for the treatment of specific pathophysiological states (28, 29). However, to date no compounds capable of delivering CO therapeutically have been identified.

U.S. Pat. No. 5,882,674 proposes administration of CO via transdermal delivery systems containing metal carbonyl complexes such as iron pentacarbonyl and iron enneacarbonyl. However, since this document provides no experimental data, and no description of specific devices, it is not clear how this proposal can be made to work. In particular it is not stated whether the iron carbonyl complex is intended to be absorbed from the patch, to release CO within the body, or whether the complex breaks down within the patch to release CO which then enters the bloodstream after absorption through the skin. If, and to the extent that, this document is considered to make available pharmaceutical devices, compositions and methods for the practical and effective delivery of carbon monoxide in vivo, such devices, compositions and methods are excluded from the scope of the present invention.

Amongst literature relating to metal carbonyls, WO98/48848 describes facial metal tricarbonyl compounds and their use in the labelling of biologically active substrates. The metals, preferably radionuclides, are of Group 7, the metals identified being Mn, $^{99}$Tc, $^{186}$Re and $^{188}$Re. The compounds fac-$[M(CO)_3(OH_2)_3]^+$ where M is the metal are proposed for labelling of biologically active substrates, as a result of which metal carbonyl compounds having a variety of biologically active ligands are obtained. In the examples radioactive Tc is used. The document describes preparation of diagnostic and therapeutic compositions but no therapeutic composition is specifically disclosed, nor is any treatment of any condition by therapy mentioned. There is no disclosure of use of the compounds for delivering carbon monoxide to physiological targets. If, and to the extent that, this document is regarded as disclosing a therapeutic use or mode of therapeutic administration of the carbonyl compounds, that subject matter is excluded from the scope of the present invention. Preferably the present invention excludes use of the facial carbonyl compounds disclosed in this document in any event.

WO 91/01128 and WO 91/01301 describe compositions for treating skin to repair the effects of photoaging by topical application or to treat acne or psoriasis by topical or oral administration. The active compounds are polyene esters and iron carbonyl complexes thereof. Specifically the iron of iron tri-carbonyl is coordinated to the polyene chain. No reason for including the iron carbonyl is mentioned. Insofar as therapeutic uses or compositions of carbonyl compounds are disclosed in these two documents, such uses and compositions are specifically excluded from the scope of the present invention.

WO 98/29115 describes compositions and methods for relaxing smooth muscle in a warm-blooded animal by administering certain transition metal nitrosyl compounds. Treatments of hypertension, angina pectoris, congestive heart failure and impotence are mentioned.

Some of the compounds contain, in addition to NO, CO as a ligand. Specifically the CO-containing compound has the formula $L_3M(NO)_yX_{3-y}$ where L is a two-electron Lewis base or $L_3$ is a six-electron Lewis base, M is a Group 6 or 8 transition metal and when y is 1, X is carbon monoxide. The essential teaching of this document is concerned with the therapeutic effect of nitrosyl complexes. There is no disclosure that the CO ligand, when present, has any therapeutic effect by delivery of CO to a physiological target. The CO-containing metal nitrosyl complexes disclosed in it are excluded from the novel metal carbonyls of the present invention and their uses for treatments mentioned are also excluded from the present invention. Preferably transition metal nitrosyl complexes containing CO are excluded from the scope of the present invention in any event.

HU-B-211084 describes a composition, which is for oral administration, for the fortification of bones containing calcium phosphate, at least one calcium salt of an organic acid and optionally iron pentacarbonyl. The present invention does not extend to the use of iron pentacarbonyl in combination with calcium compounds as specified in this document in connection with the therapeutic uses and modes of administration described there, and preferably does not extend to the use of iron carbonyls and complexes including iron and CO in combination with calcium phosphates and/or calcium salts of organic acids in any event.

WO 95/05814 (U.S. Pat. No. 6,284,752) and WO 00/56743 both disclose a very wide range of metal complexes, for use in treatment of disease relating to the overproduction of reactive oxygen species, particularly overproduction of NO. The stated aim is to modulate NO levels in the body by scavenging, or removing, NO in situ. The ex-vivo test data are stated to show that vasoconstriction is a direct result of the removal of endogenous nitric oxide. Carbon monoxide is mentioned as a possible ligand, but no example of a complex containing carbon monoxide is given and no effect is attributed to CO. Insofar as these documents are considered to disclose practical use of a complex containing CO for the specified purpose, such use does not form part of the present invention.

SUMMARY OF THE INVENTION

As exemplified by the experimental data detailed below, the present inventors have found that metal carbonyl compounds can be used to deliver CO to a physiological target so as to provide physiological effect.

Accordingly the present invention provides a pharmaceutical composition, for delivery of carbon monoxide to a physiological target, comprising a metal carbonyl compound or pharmaceutically acceptable salt thereof and at least one pharmaceutically acceptable carrier, wherein the metal carbonyl makes available CO suitable for physiological effect by at least one of the following means:

1) CO derived by dissociation of the metal carbonyl is present in the composition in dissolved form;
2) on contact with a solvent the metal carbonyl releases CO;
3) on contact with a tissue, organ or cell the metal carbonyl releases CO;
4) on irradiation the metal carbonyl releases CO.

Certain metal carbonyl compounds are capable of releasing CO on contact with a suitable solvent. When the pharmaceutical composition is to be administered in liquid form, this solvent may form a component part of the pharmaceutical composition. Thus in this aspect of the invention, the pharmaceutical composition contains CO derived from the metal carbonyl in dissolved form.

The conditions under which the carbonyl compound is dissolved in the solvent during preparation of the pharmaceutical may be controlled such that the CO thus released is retained in solution. This may be facilitated where an equilibrium exists between the dissociated components and the undissociated carbonyl.

The dissociated components of the parent carbonyl may themselves be metal carbonyl complexes capable of releasing further CO. For example, when $[Ru(CO)_3Cl_2]_2$ is dissolved in DMSO, CO is liberated into solution, and a mixture of tri-carbonyl and di-carbonyl complexes is formed, and these themselves may be capable of releasing further CO.

In a further aspect of the invention, the pharmaceutical composition may not itself contain dissolved CO, but may be prepared such as to release CO on contact with a suitable solvent or medium. For example, the composition may contain a metal carbonyl compound capable of releasing CO on contact with water, e.g. on contact with an aqueous physiological fluid, such as blood or lymph. Alternatively, the pharmaceutical composition may be intended to be dissolved in water prior to administration. Such pharmaceutical compositions may be prepared in solution or in solid form, such as in tablet form. If they are in solution form, they will typically be prepared in a solvent which does not support dissociation of the metal carbonyl compound, such that release of CO takes place only on contact with the appropriate solvent.

Alternatively or additionally, release of CO from the complex can be stimulated by reaction with a ligand in solution which for example replaces one of the ligands of the complex leading to loss of CO from the complex.

In another aspect of the invention the pharmaceutical composition may contain a metal carbonyl compound which releases CO on contact with a tissue, organ or cell. It is shown below that certain metal carbonyl compounds do not release CO to solution but are nevertheless capable of releasing CO to physiological cellular materials or tissues, such as vascular endothelium. For example, $[Fe(SPh)_2(2,2'-bipyridine)(CO)_2]$ is shown below not to release CO to myoglobin in solution, but is nevertheless capable of promoting dilatation of pre-contracted aortic rings. Without wishing to be limited by any particular theory, it is thought that CO may be released from such compounds as a result of an oxidation-reduction reaction, mediated by cellular components such as cytochromes.

However the invention is not limited to a redox reaction as a mechanism for CO release, since loss of at least a first CO from the complex may occur without redox.

In a further aspect of the invention, the pharmaceutical composition may contain a metal carbonyl compound which releases CO on irradiation. The compound may be irradiated prior to administration, for example to produce a solution of dissolved CO, or may be irradiated in situ after administration. It is contemplated that such compositions may be used to provide controlled, localised release of CO. For example a pharmaceutical composition of this type may be administered during surgery, and CO released specifically at a site in need thereof, e.g. to induce vasodilation, by localised irradiation by means of a laser or other radiant energy source, such as UV rays.

Typically the pharmaceutical compositions of the present invention release CO such as to make it available to a therapeutic target in dissolved form. However, in some circumstances CO may be released from a metal carbonyl directly to a non-solvent acceptor molecule.

It will be apparent that pharmaceutical compositions according to the present invention may be capable of delivering CO therapeutically through one or more of the above described modes of action.

Typically the metal carbonyl compound comprises a complex of a transition metal, preferably a transition metal from group 7 or groups 8 to 10 (in this specification the groups of the periodic table are numbered according to the IUPAC system from 1 to 18). The number of carbonyl ligands is not limited, provided at least one carbonyl ligand is present. The preferred metals are transition metals of lower molecular weight, in particular Fe, Ru, Mn, Co, Ni, Mo and Rh. Two other metals which may be used are Pd and Pt. In the metal carbonyl complexes used in the invention, the metal is typically in a low oxidation state, i.e. O, I or II. For the metals preferred, the oxidation states are typically not higher than $Fe^{II}$, $Ru^{II}$, $Mn^{I}$, $CO^{II}$ preferably $Co^{I}$, $R^{III}$ preferably $Rh^{I}$, $Ni^{II}$, $Mo^{II}$. The metal is preferably not a radionuclide. Fe is one particularly suitable metal, since Fe is present in quantity in mammals.

The metal carbonyl compounds may be regarded as complexes, because they comprise CO groups coordinated to a metal centre. However the metal may be bonded to other groups by other than coordination bonds, e.g. by ionic or covalent bonds. Thus groups other than CO which form part of the metal carbonyl compound need not strictly be "ligands" in the sense of being coordinated to a metal centre via a lone electron pair, but will be referred to herein as "ligands" for ease of reference.

Thus, the ligands to the metal may all be carbonyl ligands, as e.g. in $[Mn_2(CO)_{10}]$. Alternatively, the carbonyl compound may comprise at least one modulatory ligand. By this is meant a ligand which is not CO, but which modulates a particular property of the complex, such as the tendency to release CO, solubility, hydrophobicity, stability, electrochemical potential, etc. Thus suitable choices of ligand may be made in order to modulate the behaviour of the compound. For example it may be desirable to modulate the solubility of the compound in organic and/or aqueous solvents, its ability to cross cell membranes, its rate of release of CO on contact with a particular solvent or cell type, or on irradiation, etc.

Such ligands are typically neutral or anionic ligands, such as halide, or derived from Lewis bases and having N, P, O or S or a conjugated carbon group as the coordinating atom(s). Preferred coordinating atoms are N, O and S. Examples include, but are not limited to, sulfoxides such as dimethylsulfoxide, natural and synthetic amino acids and their salts for example, glycine, cysteine, and proline, amines such as $NEt_3$ and $H_2NCH_2CH_2NH_2$, aromatic bases and their analogues, for example, bi-2,2'-pyridyl, indole, pyrimidine and cytidine, pyrroles such as biliverdin and bilirubin, drug molecules such as YC-1 (2-(5'-hydroxymethyl-2'-furyl)-1-benzylindazole), thiols and thiolates such as EtSH and PhSH, chloride, bromide and iodide, carboxylates such as formate, acetate, and oxalate, ethers such as $Et_2O$ and tetrahydrofuran, alcohols such as EtOH, and nitriles such as MeCN. Particularly preferred are coordinating ligands, such as amino acids, which render the carbonyl complex stable in aqueous solution. Other possible ligands are conjugated carbon groups, such as dienes. One class of ligands which can provide metal carbonyl compounds of use in this invention is cyclopentadiene $(C_5H_5)$ and substituted cyclopentadiene. The substituent group in substituted cyclopentadiene may be for example an alkanol, an ether or an ester, e.g. —$(CH_2)_n$OH where n is 1 to 4, particularly —$CH_2OH$, —$(CH_2)_n$OR where n is 1 to 4 and R is hydrocarbon preferably alkyl of 1 to 4 carbon atoms and —$(CH_2)_n$OOCR where n is 1 to 4 and R is hydrocarbon preferably alkyl of 1 to 4 carbon atoms. The preferred metal in such a cyclopentadiene or substituted cyclopentadiene carbonyl complex is Fe.

Preferably the cyclopentadiene carbonyl complex is cationic, being associated with an anion such as chloride.

As mentioned above certain metal nitrosyl complexes disclosed in WO 98/29115 and their uses disclosed are excluded from the present invention, and preferably the invention does not extend to metal carbonyl complexes containing NO (nitrosyl) in any event. Furthermore as mentioned above certain iron carbonyl complexes disclosed in WO 91/01128 and WO 91/01301 and their uses disclosed therein are excluded from the present invention. Preferably the invention does not extend to topical or oral administration of iron carbonyl polyene complexes, nor to these complexes in themselves.

A further exclusion from the present invention are the Mn and radionuclide complexes disclosed in WO 98/48848. Preferably the present invention excludes therapeutic use of these Mn complexes. Preferably the invention excludes carbonyls of radioactive metals, in any case.

CO is suggested to act at least in part through the stimulation of guanylate cyclase activity. Thus the metal carbonyl compound may desirably comprise ligands which modulate the effect of CO on guanylate cyclase.

For example, the drug YC-1 (3-(5'-hydroxymethyl-2'-furyl)-1-benzylindole) is thought to enhance stimulation of guanylate cyclase by CO. Thus incorporation of ligands such as YC-1 or derivatives thereof into the metal carbonyl compounds can alter or enhance the biological effects of the released CO.

Thus the properties of pharmaceutical compositions of the present invention may be tailored as required by appropriate choice of metal centres and number and type of associated ligands in the metal carbonyl compound.

The metal carbonyl compound may further comprise a targeting moiety, to facilitate release of CO at an appropriate site. The targeting moiety is typically capable of binding a receptor on a particular target cell surface, in order to promote release of CO at the required site. The targeting moiety may be a part of a modulating ligand capable of binding to a receptor found on the surface of the target cells, or may be derived from another molecule, such as an antibody directed against a particular receptor, joined to the complex by a suitable linker.

The present invention also provides a pharmaceutical composition for delivery of CO, comprising as active ingredient a compound of the formula $M(CO)_xA_y$ where x is at least one, y is at least one, M is a metal, A is an atom or group bonded to M by an ionic, covalent or coordination bond, and, in the case where y>1, each A may be the same or different, or a pharmaceutically acceptable salt of such a compound. Typically, M is a transition metal, particularly of group 7 or groups 8 to 10, and A may be selected from halogens, groups having N, P, O or S atoms providing lone electron pairs for coordination bonding to M, and conjugated carbon groups. More details of preferred metals and ligands are given above. The carbonyl complex should be pharmaceutically acceptable, in particular non-toxic or of acceptable toxicity at the dosage levels envisaged.

The pharmaceutical compositions of the present invention typically comprise a pharmaceutically acceptable excipient, carrier, buffer, stabiliser or other materials well known to those skilled in the art. Such materials should be non-toxic and should not interfere unduly with the efficacy of the active ingredient. The precise nature of the carrier or other material may depend on the route of administration, e.g. oral, intravenous, subcutaneous, nasal, intramuscular, intraperitoneal, or suppository routes.

Pharmaceutical compositions for oral administration may be in tablet, capsule, powder or liquid form. A tablet may include a solid carrier such as gelatin or an adjuvant or a slow-release polymer. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Pharmaceutically acceptable amounts of other solvents may also be included, in particular where they are required for dissolving the particular metal carbonyl compound contained in the composition.

For intravenous, cutaneous or subcutaneous injection, or injection at the site of affliction, the active ingredient will typically be in the form of a parenterally acceptable solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. Delivery systems for needle-free injection are also known, and compositions for use with such systems may be prepared accordingly.

Administration is preferably in a prophylactically effective amount or a therapeutically effective amount (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

When formulating pharmaceutical compositions according to the present invention, the toxicity of the active ingredient and/or the solvent must be considered. The balance between medical benefit and toxicity should be taken into account. The dosages and formulations of the compositions will typically be determined so that the medical benefit provided outweighs any risks due to the toxicity of the constituents.

There is further provided a method of introducing CO to a mammal comprising the step of administering a pharmaceutical composition according to the present invention. CO is thought to act at least in part through stimulation or activation of guanylate cyclase. CO is thought to have functions as, inter alia, a neurotransmitter and a vasodilating agent. Accordingly there is provided a method of delivering CO to a mammal for stimulation of guanylate cyclase activity. There is further provided a method of delivering CO to a mammal for stimulating neurotransmission or vasodilation. However the present applicants do not wish to be bound by theory and do not exclude the possibility that CO operates by other mechanisms.

The heme oxygenase 1 (HO-1) pathway is thought to represent a pivotal endogenous inducible defensive system against stressful stimuli including UVA radiations, carcinogens, ischaemia-reperfusion damage, endotoxic shock and several other conditions characterised by production of oxygen free radicals (30-32). The protective effect of HO-1 is attributed to the generation of the powerful antioxidants biliverdin and bilirubin and the vasoactive gas CO. Expression of HO-1 has been linked with cardiac xenograft survival (33), suppression of transplant arteriosclerosis (34) and amelioration of post-ischemic myocardial dysfunction (35). HO-1 has also been directly implicated in the resolution phase of acute inflammation in rats (36). Other pathological situations, such as haemorrhagic shock in brain and liver as well as sepsis (37-39), are characterized by induction of the HO-1 gene, which seems to play a crucial role in counteracting the vascular dysfunction caused by these pathophysiological states. Increased generation of CO as a consequence of HO-1 induction markedly affects vessel contractility and diminishes acute hypertension in the whole organism (23, 40). Exposure of animals to ambient air containing low concentrations of CO or transfection of the HO-1 gene results in protection against hyperoxia-induced lung injury in vivo, a mechanism mediated by attenuation of both neutrophil inflammation and lung apoptosis (cell death) (41, 42). Exogenous CO gas also has the ability to suppress pro-inflammatory cytokines and modulate the expression of the anti-inflammatory molecule, IL-10, both in vitro and in vivo (43). Therefore administration of CO in accordance with the invention may be used for treatment of any of these conditions, for modulation of inflammatory states and regression of other pathophysiological conditions including cancer.

Accordingly there is provided a method of introducing CO to a mammal comprising the step of administering a pharmaceutical composition according to the present invention, for treatment of hypertension, such as acute, pulmonary and chronic hypertension, radiation damage, endotoxic shock, inflammation, inflammatory-related diseases such as asthma and rheumatoid arthritis, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome.

The present invention also provides the use of a metal carbonyl compound as herein described in the manufacture of a medicament for delivering CO to a physiological target, particularly a mammal, to provide a physiological effect, e.g. for stimulating neurotransmission or vasodilation, or for treatment of any of hypertension, such as acute, pulmonary and chronic hypertension, radiation damage, endotoxic shock, inflammation, inflammatory-related diseases such as asthma and rheumatoid arthritis, hyperoxia-induced injury, apoptosis, cancer, transplant rejection, arteriosclerosis, post-ischemic organ damage, myocardial infarction, angina, haemorrhagic shock, sepsis, penile erectile dysfunction and adult respiratory distress syndrome. Such medicaments may be adapted for administration by an oral, intravenous, subcutaneous, nasal, inhalatory, intramuscular, intraperitoneal or suppository route. Preferably the present invention excludes delivery of a metal carbonyl or a decomposition product thereof to an organism through the skin or mucosa.

The invention further provides use of the metal carbonyls here described in treatment, e.g. by perfusion, of a viable mammalian organ extracorporeally, e.g. during storage and/or transport of an organ for transplant surgery. For this purpose, the metal carbonyl is in dissolved form, preferably in an aqueous solution. The viable organ may be any tissue containing living cells, such as a heart, a kidney, a liver, a skin or muscle flap, etc.

The invention also consists in a metal carbonyl compound of the formula $$M(CO)_x A_y B_z \text{ where}$$

M is Fe, Co or Ru, x is at least one, y is at least one, z is zero or at least one, each A is a ligand other than CO and is monodentate or polydentate with respect to M and is selected from the amino acids alanine
arginine
asparagine
aspartic acid
cysteine
glutamic acid
glutamine
glycine
histidine
isoleucine
leucine
lysine
methionine
phenylalanine
proline
serine
threonine
tryptophan
tyrosine
valine
$O(CH_2COO)_2$ and
$NH(CH_2COO)_2$, and B is optional and is a ligand other than CO,
excluding $Fe(CO)_xA_y$, where A is cysteine or an ester of cysteine and $Ru(CO)_nA_y$ where A is proline.

x is preferably 3, y is preferably 1 and z is preferably 1.

The term amino acid here used includes the species obtained by loss of the acidic hydrogen, such as glycinato.

$B_2$ represents one or more optional other ligands. There are no particular limitations on B, and ligands such as halides, e.g. chloride, bromide, iodide, and carboxylates, e.g. acetate may be used.

M is selected from Fe, Ru and Co. These metals are preferably in low oxidation states, as described above.

Use of the known iron compounds $[Fe(SPh)_2(2,2'-bipyridine)(CO)_2]$ and $[Fe(SPh)_2(NH_2CH_2CH_2NH_2)(CO)_2]$ is also envisaged in this invention.

It is further considered that, in place of the metal carbonyl compounds discussed above, the pharmaceutical compositions of the present invention may comprise oxalate compounds, formic acid, or formate compounds, which may likewise deliver CO to a physiological target. For example, bis-(2,4-dinitrophenyl) oxalate is known to decompose in water to liberate CO into solution. Therefore the present invention further provides a pharmaceutical composition, for delivery of carbon monoxide to a physiological target, comprising formic acid, a formate, a formate ester or amide, an oxalate, or an oxalate ester or amide, or a pharmaceutically acceptable salt thereof and at least one pharmaceutically acceptable carrier, wherein the formic acid, formate or oxalate or amide or ester makes available CO suitable for physiological effect.

It is thought that the nitrophenyl groups of bis-(2,4-dinitrophenyl) oxalate are good leaving groups, because of the electron-withdrawing effects of the nitro groups, and that this may promote the decomposition of the oxalate to yield CO.

It is therefore considered that oxalates or formates having in which the acid groups are linked, e.g. by an ester bond, to aromatic groups with electron-withdrawing substituents, such as tosyl groups, are particularly suitable for use in pharmaceutical compositions according to the present invention.

There is further provided a method of introducing carbon monoxide to a mammal comprising the step of administering a pharmaceutical composition comprising formic acid, a formate, a formate ester or amide or an oxalate, an oxalate ester or amide, or a pharmaceutically acceptable salt thereof, and at least one pharmaceutically acceptable carrier.

All the above discussion and disclosure relating to metal carbonyl compounds is also considered to relate to formic acid, formates, oxalates and formate or oxalate amides and esters.

Throughout this application, references to medical treatment are intended to include both human and veterinary treatment, and references to pharmaceutical compositions are accordingly intended to encompass compositions for use in human or veterinary treatment.

INTRODUCTION OF THE DRAWINGS

Experimental data illustrating the present invention will now be described by reference to the accompanying figures, in which:

FIGS. 9a to 9f are tables presenting CO release data of metal carbonyl complexes.

EMBODIMENTS OF THE INVENTION AND EXPERIMENTAL DATA

For the experiments here described, iron pentacarbonyl, $[Fe(CO)_5]$, dimanganese decacarbonyl, $[Mn_2(CO)_{10}]$, tricarbonyldichlororuthenium (II) dimer, $[Ru(CO)_3Cl_2]_2$, and ruthenium(III) chloride hydrate, $RuCl_3$, were purchased from Sigma-Aldrich Company Ltd. (Poole, Dorset, UK). Other carbonyl complexes have been synthesized, as described below. Stock solutions of metal carbonyl complexes were prepared fresh prior to each experiment by dissolving the compounds in dimethyl sulfoxide (DMSO), water or saline. Hemin (ferriprotoporphyrin IX chloride) and tin protoporphyrin IX (SnPPIX) were from Porphyrin Products Inc. (Logan, Utah, USA). Stock solutions of both porphyrins were prepared by dissolving the compounds in 0.1 M NaOH and then adjusting the pH to 7.4 by addition of 0.01 M phosphate buffer. The guanylate cyclase inhibitor, [1H-[1,2,4]Oxadiazole[4,3-a]quinoxalin-1-one] (ODQ), was obtained from Alexis Corporation (Bingham, Nottingham, UK) and polyclonal rabbit anti-HO-1 antibodies were purchased from Stressgen (Victoria, Canada). Horse heart myoglobin, $N^G$-nitro-L-arginine methyl ester (L-NAME) and all other reagents were from Sigma, unless otherwise specified.

All data are expressed as mean±s.e.m. Differences between the groups analysed were assessed by the Student's two-tailed t-test, and an analysis of variance (ANOVA) was performed where more than two treatments were compared. Results were considered statistically significant at P<0.05.

A. Detection of CO Liberated from Transition Metal Carbonyl Complexes.

The release of CO from metal carbonyl complexes was assessed spectrophotometrically by measuring the conversion of deoxymyoglobin (deoxy-Mb) to carbonmonoxy myoglobin (MbCO). MbCO has a distinctive absorption spectrum between 500 and 600 nm, and changes at 540 nm were used to quantify the amount of CO liberated. Myoglobin solutions (66 µM final concentration) were prepared freshly by dissolving the protein in 0.04 M phosphate buffer (pH 6.8). Sodium dithionite (0.1%) was added to convert myoglobin to deoxy-Mb prior to each reading. All the spectra were measured using a Helios α spectrophotometer.

Figure 1:
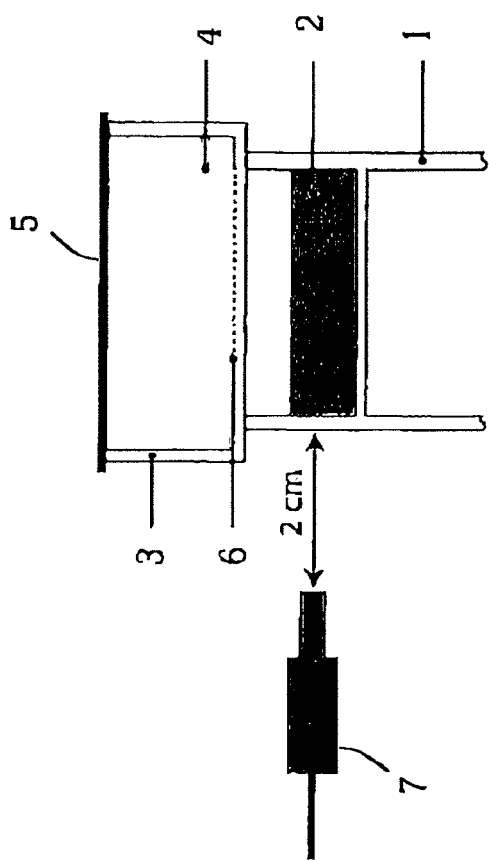
FIG. 1 shows apparatus for measuring release of CO by metal carbonyl complexes on irradiation and structures of $[Mn_2(CO)_{10}]$ and $[Fe(CO)_5]$.
Figure 1:
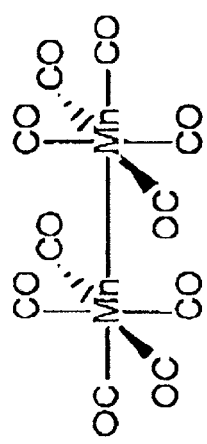
Figure 1:
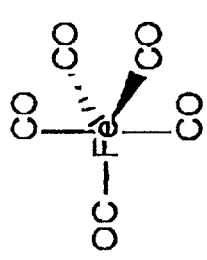

Direct addition of iron pentacarbonyl, $[Fe(CO)_5]$, or dimanganese decacarbonyl, $[Mn_2(CO)_{10}]$, to myoglobin solutions did not result in any appreciable formation of carbonmonoxy myoglobin (MbCO) over time (data not shown). This is consistent with the notion that these two transition metal carbonyl complexes do not release CO unless stimulated by light (44, 45). Therefore release of CO was induced by exposing these metal carbonyl complexes to a cold light source and allowing the gas to diffuse through a membrane before reacting with myoglobin as shown in FIG. 1.

Five hundred microliters of iron pentacarbonyl ($[Fe(CO)_5]$, 99.9%) or 1 ml of dimanganese decacarbonyl ($[Mn_2(CO)_{10}]$, 13 mM in DMSO) (see also chemical structure) were placed as carbonyl solution 2 in a plastic tube 1. A cell culture insert 3 (Costar) was sealed on top in order to create two separate chambers with a 0.6 cm air space between the solution 2 and an insert membrane 6 (Anapore™ 0.4 µm). 1.5 ml of deoxy-Mb solution (66 µM) was placed in the insert which was covered with Parafilm™ 5. The carbonyl solution was then exposed to cold light from a source 7 to stimulate CO release, allowing the gas to diffuse through the membrane 6 into the myoglobin solution 4. Aliquots of the myoglobin solution 4 were taken at different times and the conversion of deoxy-Mb to MbCO measured spectrophotometrically.

Figure 2A:
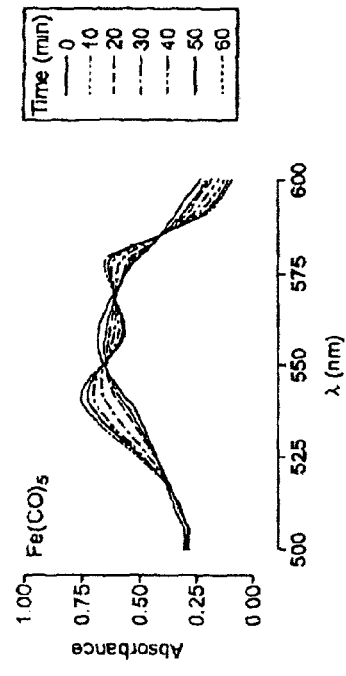
FIG. 2 shows deoxy-myoglobin and CO-myoglobin absorption spectra.
Figure 2B:
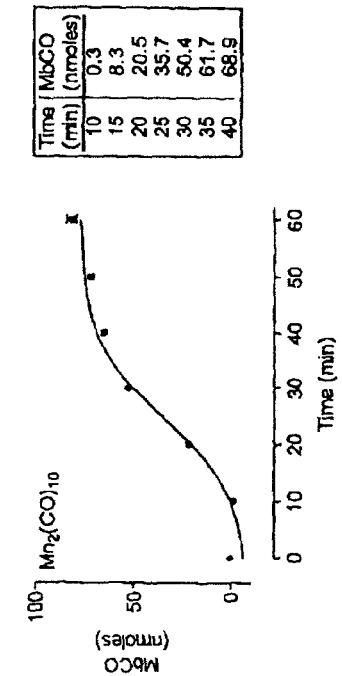
Figure 2C:
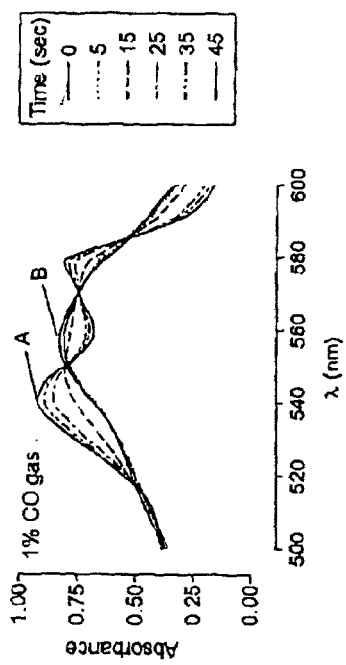
Figure 2D:
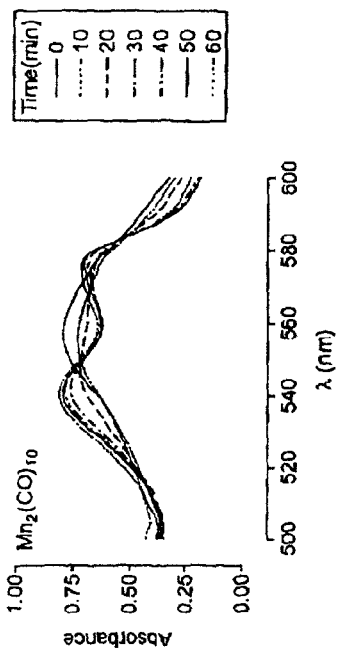

The spectral change on transition from deoxy-Mb to MbCO was measured by bubbling CO gas to a solution of deoxy-Mb (FIG. 2a). Upon illumination, $[Fe(CO)_5]$ and $[Mn_2(CO)_{10}]$ produced a similar change in the absorbance spectrum of myoglobin, with a gradual increase in MbCO formation observed over time; in both cases the distinctive identified spectra were the ones typical of MbCO (FIGS. 2b and 2c). Under the experimental conditions used, a complete saturation of the myoglobin solution was achieved by $[Mn_2(CO)_{10}]$ (13 µmol/ml) in approximately 40 min of continuous exposure to light (FIG. 2d).

Various metal carbonyl complexes were tested for their ability to elicit MbCO formation when added directly to a deoxy-Mb solution. To different extents, $[Ru(CO)_3Cl_2]_2$, $[Ru(CO)_2(DMSO)_2Cl_2]$, $[Ru(CO)_3Cl_2(cytosine)]$ and $[Bu(CO)_3(glycinate)Cl]$ all released CO when added directly to the Mb solution. No MbCO was detected in the case of $[Fe(SPh)_2(2,2'-bipyridine)(CO)_2]$ and $[Fe(SPh)_2(H_2NCH_2CH_2NH_2)(CO)_2]$, but as shown below both these compounds provided a vasodilatory effect.

Figure 2E:
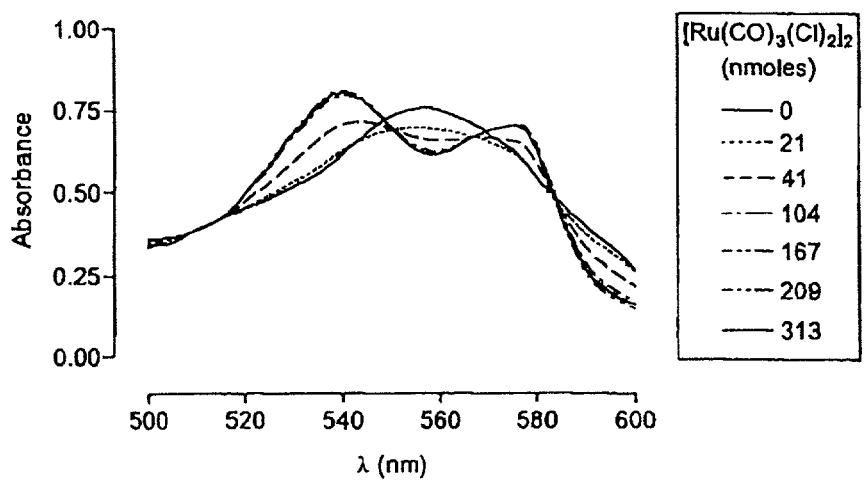
Figure 2F:
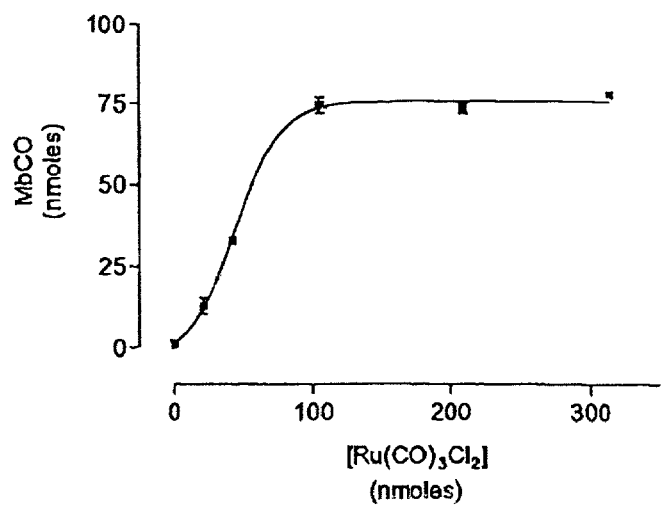

Data for the tricarbonyldichlororuthenium (II) dimer $[Ru(CO)_3Cl_2]_2$ are shown in FIG. 2e. The metal carbonyl complex was solubilized in DMSO (9.7 mM stock solution), aliquots of 2 to 32 µl were added directly to 1 ml of deoxy-Mb solutions (66 µM) and absorption spectrum determined immediately after mixing the samples by inversion. A linear regression analysis of the saturation curve of MbCO revealed that for each mole of $[Ru(CO)_3Cl_2]_2$ approximately 0.7 moles of CO are liberated (FIG. 2f).

Further data on release of CO measured by the same test procedure is described in section H below.

B. NMR Studies of $[Ru(CO)_3Cl_2]_2$

Figure 3:
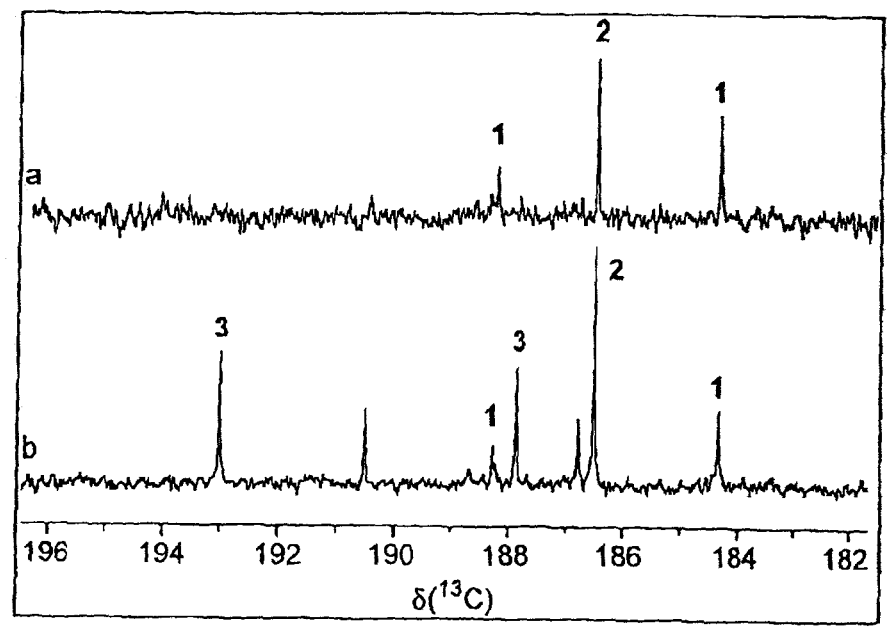
FIG. 3 shows NMR spectra illustrating the dissolution of $[Ru(CO)_3Cl_2]_2$ in DMSO.
Figure 3:
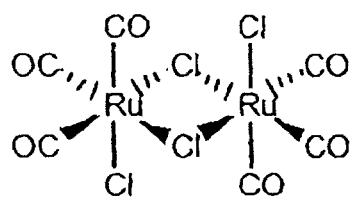
Figure 3:
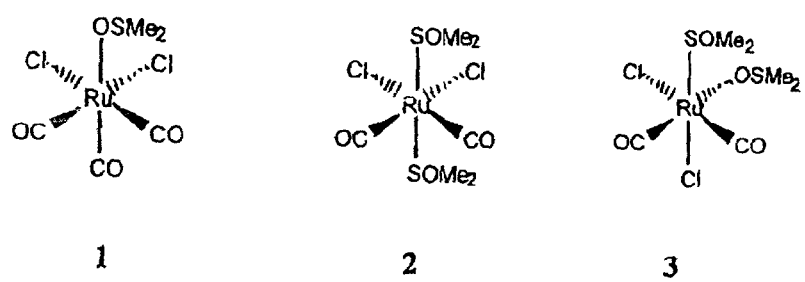

Further studies were conducted on the chemistry of transition metal carbonyls using NMR spectroscopy. The $^{13}C$ NMR spectrum showed that $[Ru(CO)_3Cl_2]_2$ freshly dissolved in DMSO does not exist as a dimer; in fact, two distinct sets of signals corresponding to the known tri-carbonyl (1) and di-carbonyl (2) monomers (see formulae in FIG. 3) could be identified. The NMR analysis reveals that, during the solubilization process, DMSO acts as a coordinated ligand to ruthenium thereby promoting the formation of the monomers.

FIG. 3a shows a 100.62 MHz $^{13}C\{^1H\}$ NMR spectrum taken during the first 23 min of the reaction between freshly prepared $[RuCl_2(CO)_3]_2$ and $d_6$-DMSO. The solution very slowly produced fine bubbles of a gas, presumably CO, implied by the formation of compound 2. When the experiment was repeated by dissolving initially the metal complex in DMSO and then diluting with $CDCl_3$, the assignment of the signals coincided with the published $^{13}C(CO)$ chemical shifts of fac-$[RuCl_2(CO)_3(DMSO)]$ (1, δ 183.0, 186.8), cis, cis, trans-$[RuCl_2(CO)_2(DMSO)_2]$ (2, δ 185.0) and cis, cis, cis-$[RuCl_2(CO)_2(DMSO)_2]$ (3, δ 186.0, 191.9) (46). FIG. 3b shows a 100.62 MHz $^{13}C\{^1H\}$ NMR spectrum taken after $[RuCl_2(CO)_3]_2$ in $d_6$-DMSO was warmed at 50° C. for 5 min and left to accumulate overnight. In addition to the peaks that could be assigned to compounds 1, 2 and 3, there are carbonyl signals at δ 187.9 and 190.5 due to unidentified species.

The detection of di-carbonyl monomers demonstrates that CO is liberated; the $^{13}C$ NMR spectrum also suggests that the ratio between compounds 1 and 2 is 40:60.

In sections C and D below, we refer for convenience to $[Ru(CO)_3Cl_2]_2$, but as explained here, when dissolved in DMSO other species are actually present.

C. Effect of $[Ru(CO)_3Cl_2]_2$ on Cell Viability

As there are no precedent studies on the use of metal carbonyl complexes in biological systems, it was necessary to evaluate the potential cytotoxic effect of these compounds. Therefore, the viability of cells in culture was determined after short or prolonged exposure to various concentrations of metal carbonyls.

Rat vascular smooth muscle cells were obtained from the Coriell Cell Repository (Camden, N.J., USA) and grown in Dulbecco's Minimal Essential Medium (MEM) supplemented with 20% foetal calf serum, 2×MEM vitamins, 2×MEM non-essential and essential amino acids, penicillin (100 units/ml) and streptomycin (0.1 mg/ml). Confluent cells were treated with different concentrations of metal carbonyl (introduced as DMSO solution—see section B) for various times and cell viability was assessed using a colorimetric assay kit from Promega (Madison, Wis., USA) as previously described (47) after 3 or 24 h incubation, or after 3 h exposure to the agents followed by 21 h incubation in complete media. Results are expressed as the mean±s.e.m. of 6 independent experiments and differences were considered statistically significant at P<0.05 (*).

Exposure of $[Fe(CO)_5]$ to light gradually resulted in deposition of a green-brown precipitate, and so viability studies on this metal carbonyl were not pursued. Nevertheless, $[Fe(SPh)_2(2,2'-bipyridine)(CO)_2]$ proved to elicit a marked vasodilatory effect (see below).

Figure 4A:
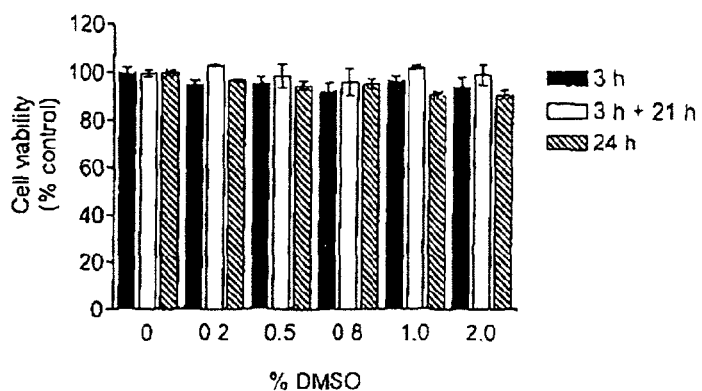
FIG. 4 shows viability data for cells treated with metal carbonyl compounds.
Figure 4B:
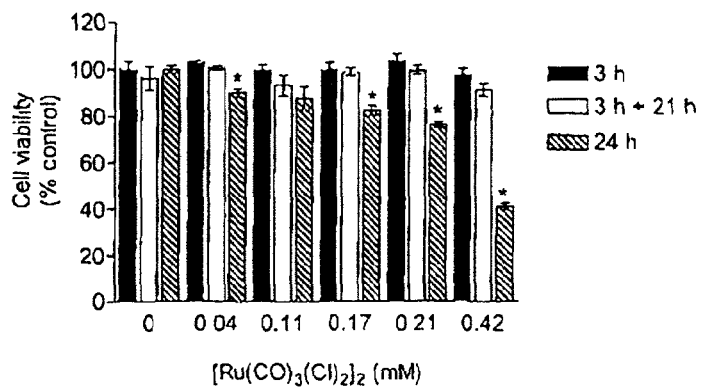

As shown in FIG. 4b, treatment of vascular smooth muscle cells for 3 h with $[Ru(CO)_3Cl_2]_2$ (0-420 µM final concentration) did not promote any detectable cytotoxicity. Similarly, cell viability was well preserved after exposure to this metal carbonyl for 3 h followed by an additional 21 h incubation in complete medium. A pronounced cytotoxic effect (>50% loss in cell viability) was only apparent after prolonged exposure (24 h) to very high concentrations (>400 µM) of [Ru(CO)$_3$Cl$_2$]$_2$.

Figure 4C:
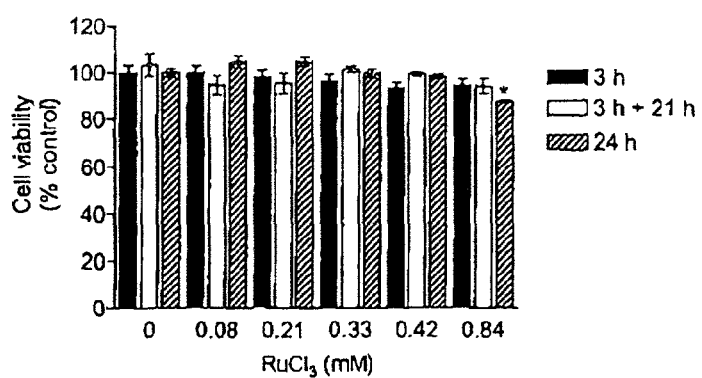

Treatment of cells with the same amounts of vehicle (DMSO) or equivalent molar concentrations of ruthenium (RuCl$_3$) did not cause any appreciable decrease in cell viability over time (FIGS. 4a and 4c, respectively) indicating that neither the vehicle nor the metal are responsible for the observed cytotoxic effect of [Ru(CO)$_3$Cl$_2$]$_2$.

In the case of [Mn$_2$(CO)$_{10}$] (0-100 µM), no major cytotoxicity on smooth muscle cells was detected after exposure for 24 h in complete medium (data not shown).

D. Vasodilatory Effect of CO Released from [Ru(CO)$_3$Cl$_2$]$_2$

It has previously been demonstrated that increased endogenous CO as a result of HO-1 induction in rat aortas markedly attenuates vasoconstriction (23). To investigate whether CO released from metal carbonyl complexes evokes specific biological activities, we first assessed the effect of these complexes on vessel contractility using the isolated aortic ring model.

Transverse ring sections of thoracic aorta were isolated from male Lewis rats and suspended under a 2 g tension in an organ bath containing oxygenated Krebs-Henseleit buffer at 37° C. as previously described (23). The relaxation response to cumulative doses of metal carbonyl (dissolved in DMSO—see section 2) was assessed in aortic rings pre-contracted with phenylephrine (3 µM). Control rings were similarly treated by adding equal doses of DMSO (vehicle) to the organ bath. Results are shown in Table 1 and FIG. 5.

Figure 5:
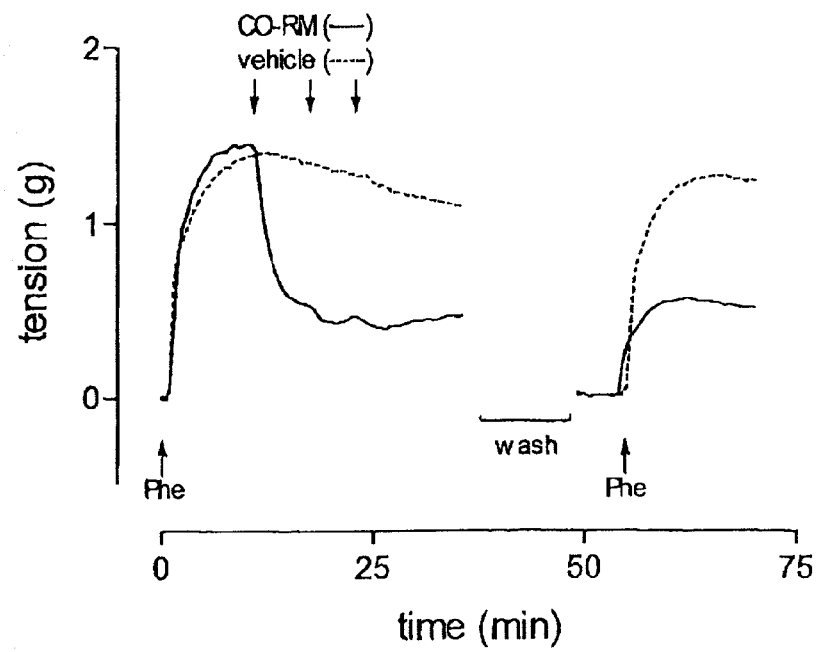
FIG. 5 shows relaxation of aortic rings on treatment with metal carbonyl complexes.

As shown in FIG. 5, consecutive additions of [Ru(CO)$_3$Cl$_2$]$_2$ (222 µM final concentration) to aortic rings pre-contracted with phenylephrine elicited a rapid and significant vasodilatation (P<0.05); the extent of relaxation was already pronounced after the first addition of the compound (45% more than control). Interestingly, after extensive washing, the phenylephrine-induced contraction was completely restored in control but not in [Ru(CO)$_3$Cl$_2$]$_2$-treated vessels indicating that this compound produces long-lasting effects.

The vasodilatory response mediated by metal carbonyls was almost totally abolished when reduced Mb (1500), which avidly binds CO, was added to the buffer. Collectively, these findings are consistent with the fact that CO released from metal carbonyls possesses vasoactive properties.

As shown in Table 1, [Ru(CO)$_2$(DMSO)$_2$Cl$_2$] also produced vasodilatation although the effect was less pronounced compared to [Ru(CO)$_3$Cl$_2$]$_2$. Interestingly, while [Ru(CO)$_3$Cl$_2$(cytosine)] did not demonstrate any effect during the time duration of this experiment, [Ru(CO)$_3$(glycinato)Cl] elicited significant vasodilatation which is consistent with the high release of CO detected with the MbCO assay. Notably, [Fe(SPh)$_2$(2,2'-bipyridine)(CO)$_2$] which did not release any detectable CO to myoglobin, was still very effective in promoting vasorelaxation. On the other hand, the effect of [Fe(SPh)$_2$(H$_2$NCH$_2$CH$_2$NH$_2$)(CO)$_2$] was less evident.

TABLE 1

| Treatment | % Relaxation | | |
|---|---|---|---|
| | 1$^{st}$ addition | 2$^{nd}$ addition | 3$^{rd}$ addition |
| Vehicle (DMSO) | 5.7 ± 0.9 | 11.4 ± 1.1 | 18.1 ± 2.5 |
| [Ru(CO)$_3$Cl$_2$]$_2$ | 49.9 ± 2.7* | 66.2 ± 3.2* | 74.1 ± 4.1* |
| [Ru(CO)$_3$Cl$_2$]$_2$ + Mb | 4.0 ± 0.9† | 8.6 ± 0.4† | 15.5 ± 0.4† |

TABLE 1-continued

| Treatment | % Relaxation | | |
|---|---|---|---|
| | 1$^{st}$ addition | 2$^{nd}$ addition | 3$^{rd}$ addition |
| [Ru(CO)$_3$Cl$_2$]$_2$ + ODQ | 7.1 ± 1.1† | 23.6 ± 3.8*† | 55.5 ± 6.9*† |
| [Ru(CO)$_2$(DMSO)$_2$Cl$_2$] | 1.6 | 16 | 35 |
| [Ru(CO)$_3$Cl$_2$(cytosine)] | 3.2 | 10.3 | 12.6 |
| [Ru(CO)$_3$(glycinato)Cl] | 36 | 66.6 | 68.3 |
| [Fe(SPh)$_2$(2,2'-bipyridine)(CO)$_2$] | 50.8 | 60.5 | 75 |
| [Fe(SPh)$_2$(H$_2$NCH$_2$CH$_2$NH$_2$)(CO)$_2$] | 11 | 24.6 | 29.3 |

*P < 0.01, compared to vehicle;
†P < 0.01 compared to [Ru(CO)$_3$Cl$_2$]$_2$.

Because CO is thought to modulate signal transduction mechanisms via increased production of cGMP, we investigated the effect of a selective inhibitor of guanylate cyclase (ODQ, 10 µM) on vessel contractility. As expected, ODQ considerably reduced the vasodilatation observed after the first two additions of [Ru(CO)$_3$Cl$_2$]$_2$; however, it is of interest that the third addition of [Ru(CO)$_3$Cl$_2$]$_2$ still elicited a substantial vasodilatory action despite the presence of ODQ. Thus, the guanylate cyclase-cGMP pathway appears to be involved in the relaxation caused by this metal carbonyl complex.

E. Expression of Heme Oxygenase in Rat Tissues

As a background to the experiments below, we conducted the following procedure to demonstrate the effect of stimulating CO production endogenously by treating animals with hemin.

For immunohistochemistry analysis, sections of heart muscles (5 µm thickness) were treated with 0.3% H$_2$O$_2$ in methanol to block endogenous peroxidase activity. Immunohistochemical staining was performed using rabbit polyclonal antibody against HO-1 (1:1000 dilution) as previously described (23). The presence of HO-1 was indicated by the development of a brown color. For Northern blot analysis, cardiac tissue was ground in a mortar under liquid nitrogen and suspended in guanidinium thiocyanate lysis buffer, Total RNA was then extracted using a modification of the method described by Chomczynski and Sacchi (49). RNA was run on a 1.3% denaturing agarose gel containing 2.2 M formaldehyde and transferred onto a nylon membrane overnight. The membrane was hybridized using [α-$^{32}$P]dCTP-labelled cDNA probes to rat HO-1 and GAPDH genes and bands analyzed using a densitometer as previously described (23, 50).

Hearts were removed from Lewis rats 24 h after treatment with vehicle (control) or hemin (75 mmol/kg, i.p.) and immunostaining for HO-1 was assessed. For Northern blot analysis, rats were treated with hemin (75 µmol/kg, i.p.) and hearts removed at different time points to assess HO-1 mRNA levels (+ve, positive control).

Figure 7:
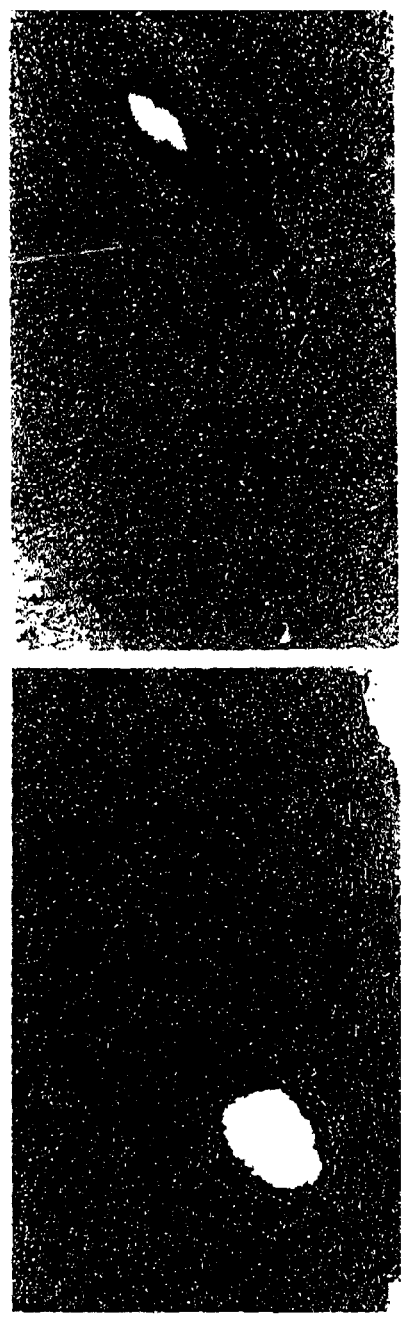
FIG. 7 shows expression of heme oxygenase 1 in rat hearts.
Figure 7:
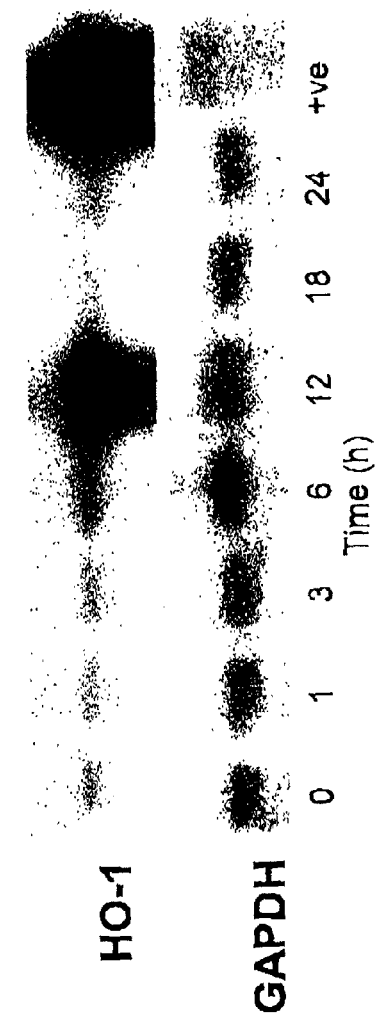

FIG. 7 confirms that HO-1 protein (7a) and mRNA (7b) are highly expressed in hearts 24 h after hemin treatment; interestingly, the immunostaining for HO-1 protein was primarily confined to the vessels of cardiac muscle (FIG. 7a, right panel).

F. Attenuation of Vasoconstriction by Metal Carbonyls in Perfused Heart

Additional experiments were conducted to determine the biological activity of metal carbonyls on vascular function in vivo and compare it with HO-1-derived CO, by monitoring their effects on changes in coronary perfusion pressure (CPP) of isolated rat hearts.

Langendorff heart preparations were performed using male Lewis rats (300-350 g) as previously described by our group (35). Hearts were excised, the aorta cannulated and retrograde perfusion was established at a constant flow of 15 ml/min using Krebs-Henseleit buffer (in mM: 119 NaCl, 4.7 KCl, 2.5 $CaCl_2$, 1.66 $MgSO_4$, 24.9 $NaHCO_3$, 1.18 $KH_2PO_4$, 5.55 glucose, 2.00 sodium pyruvate, 0.5 EGTA) bubbled with 95% $O_2$ and 5% $CO_2$ at 37° C. (pH 7.4). Coronary perfusion pressure (CPP), a parameter indicative of coronary vessel contractility, was continuously measured by a pressure transducer connected to the aortic cannula and data analyzed with an Acknowledge software (BIOPAC System Inc.).

Hearts removed either from control rats (vehicle-treated) or from animals that were pre-treated with the heme oxygenase-1 inducer hemin (75 µmol/kg, i.p.) the day before, were initially equilibrated for 20 min on the Langendorff apparatus and then perfused with L-NAME (25 µM final concentration) to elicit vasoconstriction. The extent of CPP increase by L-NAME was also monitored over time in hemin-treated animals that received a heme oxygenase inhibitor (SnPPIX, 40 µmol/kg) 1 h prior to heart excision and in control hearts that were perfused with buffer supplemented with $[Mn_2(CO)_{10}]$ (13 µM final concentration). Since $[Mn_2(CO)_{10}]$ releases CO only by photodissociation, Krebs buffer containing $[Mn_2(CO)_{10}]$ was exposed to a cold light source immediately before entering the aortic cannula.

Figure 6:
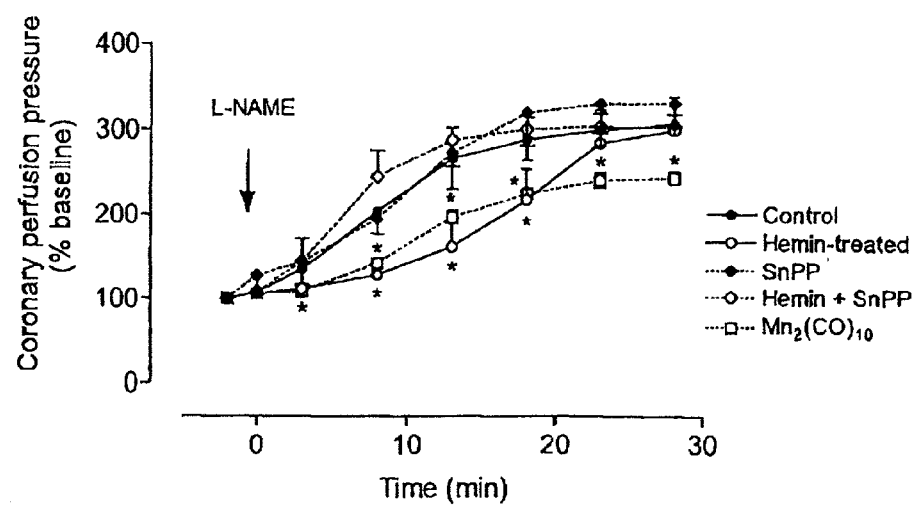
FIG. 6 shows the effects of various treatments on perfused rat hearts.

Vasoconstriction was elicited by perfusion with L-NAME and the extent of CPP increase measured over time. As shown in FIG. 6, L-NAME caused a time-dependent increase in CPP, which reached a maximum (3-fold) after 30 min. Notably, perfusion of hearts with light-stimulated $[Mn_2(CO)_{10}]$ (13 µM) significantly delayed vasoconstriction and maintained CPP at much lower levels at the end of perfusion. When the buffer containing $(Mn_2(CO)_{10})$ was not exposed to light, thus omitting the CO-induced release process, the extent of constriction mediated by L-NAME was unaffected (data not shown); in addition, perfusion with manganese chloride (negative control) had no effect on myocardial CPP (data not shown).

The effect observed with $[Mn_2(CO)_{10}]$ could be similarly reproduced by induction of HO-1 in heart tissue by pretreatment with hemin. It has previously been reported that treatment of rats with hemin results in increased production of cardiac bilirubin, which is equimolar to endogenously generated CO (35). The rise in CPP mediated by L-NAME in hemin-treated hearts was markedly attenuated ($P<0.05$), to an extent similar to that produced by $[Mn_2(CO)_{10}]$ (FIG. 6); predictably, the effect of hemin was completely reversed by tin protoporphyrin IX (SnPPIX), a heme oxygenase inhibitor. Thus, the vasoactive properties of the HO-1/CO pathway can be simulated by $[Mn_2(CO)_{10}]$.

Results are means±s.e.m. of 6 independent experiments. * $P<0.05$ vs. vehicle-treated group (control).

G. Animal Studies

Since it has previously been reported that HO-1-derived CO also prevents acute hypertension in vivo (40), experiments were performed to examine the effectiveness of metal carbonyls in regulating mean arterial pressure in animals.

Lewis rats (280-350 g) were anaesthetised by intramuscular injection of 1 ml/kg Hypnorm (fentanyl 0.315 mg/ml and fluanisone 10 mg/ml) followed 5 min later by an intraperitoneal injection of 5 mg/kg diazepam. Specially designed femoral artery and venous catheters were then surgically implanted as previously described (40). The arterial cannula was connected to a Grass pressure transducer and blood pressure monitored continuously using a polygraph recorder. Experiments were conducted on anaesthetized animals and recordings were made within 30 min of the surgical procedure.

Figure 8:
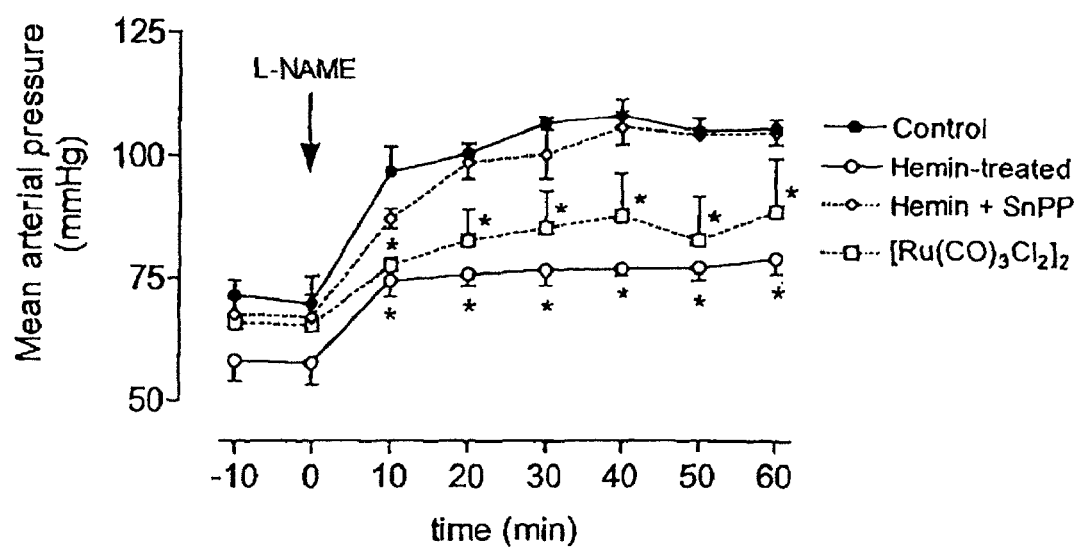
FIG. 8 shows the effects of various treatments on rat mean arterial pressure.
Figure 9F:
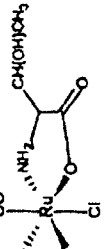
Figure 9F:
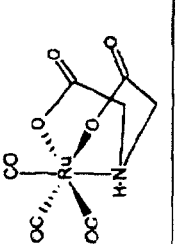
Figure 9F:
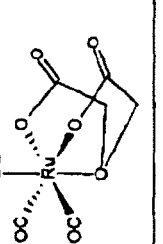
Figure 9F:
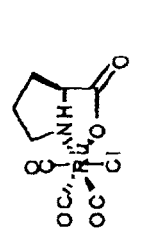

Control rats (vehicle-treated) and animals that were pre-treated with hemin (75 µmol/kg, i.p) 24 h prior to blood pressure monitoring were then administered with an intravenous injection of 30 µmol/Kg L-NAME to elicit an increase in mean arterial pressure. The extent of blood pressure increase by L-NAME was also monitored over time in hemin-treated animals that received SnPPIX (40 µmol/kg, i.p.) and in control rats previously injected with $[Ru(CO)_3Cl_2]_2$ (60 µmol/kg, i.v.). In these two groups, SnPPIX or $[Ru(CO)_3Cl_2]_2$ were administered to animals 1 h prior to L-NAME injection. Results are shown in FIG. 8.

Intravenous infusion of L-NAME in rats produced a rapid and significant increase in blood pressure ($P<0.05$); this effect was markedly suppressed by pre-treatment of animals with a single infusion of $[Ru(CO)_3Cl_2]_2$ prior to L-NAME administration. Moreover, and in analogy with the data on coronary vasoconstriction in isolated hearts, treatment of animals with hemin resulted in a significant suppression of the L-NAME-mediated hypertensive responses, which once again was totally reversed by blockade of the heme oxygenase pathway with SnPPIX. Results are the means±s.e.m. of 5 independent experiments. *$P<0.05$ vs. vehicle-treated group (control). Collectively, these in vivo findings attest a consistent and reproducible biological activity of metal carbonyls through their ability to carry and deliver CO.

H. Further Studies on CO Release

The myoglobin assay procedure of section A above was carried out on many other metal-carbonyl complexes, to determine the amount of CO release and information on the kinetics of CO release. The compounds and the results are tabulated in FIGS. 9a to 9f. The compounds include $[Ru(CO)_3 Cl_2]_2$ also tested in section A and complexes related to it. The applicants' internal reference numbers are used for convenience.

To obtain the data in FIGS. 9a to 9f the carbonyl compounds (CO-RMs) were solubilized in water or DMSO as indicated and added immediately to a solution of myoglobin (66 µM) in phosphate buffer (pH=7.4). Two different concentrations were tested for each CO-RM (20 and 40 µM) and the conversion of myoglobin to carbon monoxide myoglobin (MbCO) was measured spectrophotometrically at different time points (0, 10, and 30 min). MW=molecular weight. PPT indicates that a precipitate formed. N.D.="not detectable".

The CO release data of section A above and FIGS. 9a to 9f shows that selection of the ligands modulates CO release, both as to amount released and rate of release, permitting selection of release properties, which is important for targeting a specific biological effect.

I. Effect of CO-RM-3 ($Ru(CO)_3Cl(glycinato)$) on Systemic Blood Pressure and Heart Rate in Anaesthetised Rats Adult male Sprague-Dawley rats (280-350 g, 8-10 weeks of age) were bred in-house at the Northwick Park Institute for Medical Research (Harrow, UK). Rats were housed in groups of 3 in cages under a 12 h cycle of day/night, with free access to drinking water and fed ad libitum. All surgical procedures were performed in compliance with U.K. Home Office regulations. Rats were anaesthetised in a polycarbonate chamber in a stream of Enflurane™ (Abbot, UK) in oxygen before being transferred onto a mask and continuously supplied with Enflurane™ throughout the experiment with an anaesthetic machine (Aimed, UK). During the surgical procedure the rats were kept at a constant body temperature of 37° C. using a heat pad positioned underneath the operating surface. Specially designed femoral artery and venous catheters were then surgically implanted as previously described (see ref. 40). The catheter in the artery was connected via a luer connector and a three-way tap to a pressure transducer (Gould model P23ID, Statham, USA) for continuous mean arterial pressure (MAP) and heart rate (HR) monitoring. A purpose-built tail-cuff pressure transducer (ADInstruments, UK) was also placed on the tail of the rat and pressure transducer and tail cuff were connected to a polygraph recorder (Grass, Model 7D, Astra-med, UK) pre-calibrated in millimeters of mercury (mmHg). An analogue output provided data for a computer-based data acquisition system (PowerLab™, ADInstruments, UK). The computer-based system was set to record mean arterial pressure (MAP), in mmHg, and heart rate (HR), in beats/min (bpm), for the duration of the experiment. A period of 20 minutes was allowed after surgery during which time anaesthetic supply was adjusted so that each animal had a stable resting MAP of around 80 mmHg (n=16, mean=81.5 mmHg). Once a stable pressure had been reached, each catheter was flushed with saline containing heparin and no further changes were made to the anaesthetic supply. $Ru(CO)_3Cl$(glycinato) (CO-RM-3) was prepared in stock solutions of 20, 60 and 120 µmoles·ml$^{-1}$ by solubilizing the compound in saline. Cis-$RuCl_2(DMSO)_4$, which does not contain any carbonyl groups, was used as a 'negative control'. CO-RM-3 (or the negative control) was then infused into the animal via the femoral vein catheter as a bolus so that the final concentration infused was 10, 30 or 60 µmoles·kg$^{-1}$ body weight. Throughout the experiment MAP and HR were continuously recorded and monitored. Although concentrations of 10, 30 and 60 µmoles·kg$^{-1}$ were infused into each animal, the resulting concentrations in the animal were cumulative. Therefore, the final concentration attained in the animal was 10, 40 and 100 µmoles·kg$^{-1}$, respectively.

The results are presented in Table 2, where the data shown represents samples taken at baseline (just before infusion of the compound) and directly after administration of 10, 30 and 60 µmoles·kg$^{-1}$ of the compound. All data are mean i SEM. n=3 independent experiments. *$P<0.05$ vs. baseline.

Cis-$RuCl_2(DMSO)_4$ (control) had no significant effects on either HR or MAP at any of the concentrations used (10, 30 or 60 µmoles·kg$^{-1}$). Even after the final (60 µmoles·kg$^{-1}$) infusion of Cis-$RuCl_2(DMSO)_4$, the MAP (81±4 mmHg) and HR (256±9 bpm) were well preserved compared to baseline measurements (80±2 mmHg and 257±7 bpm, respectively). There was a marginal increase (5.5±1 mmHg) in MAP during the administration of each bolus of the compound. However, this effect is believed to be associated with a volume increase since it also occurred when saline was infused during the inserting procedure. In contrast, administration of $Ru(CO)_3$Cl(glycinato) resulted in a concentration-dependent transient decrease in MAP followed by a return to baseline over a period of 10 min; with 10, 30 and 60 µmoles·kg$^{-1}$ bolus infusions resulting in 6±2, 8±3 and 14±0.3 ($P<0.05$) mmHg decreases, respectively. As before, HR remained unchanged (253±23 bpm) compared to baseline (270±20 bpm). These data demonstrate that CO liberated from CO-RM-3 can modulate blood pressure and can be used therapeutically to control acute and chronic hypertensive responses in vivo. These data parallel the evidence that endogenous CO generated from activated heme oxygenase-1 is a potent vasodilator and suppresses acute hypertension in vivo (see ref. 23 and 40).

TABLE 2

| Compound | Baseline | | 10 µmol.kg$^{-1}$ | | 30 µmol.kg$^{-1}$ | | 60 µmol.kg$^{-1}$ | |
| --- | --- | --- | --- | --- | --- | --- | --- | --- |
| | HR (bpm) | MAP (mmHg) | HR (bpm) | MAP (mmHg) | HR (bpm) | MAP (mmHg) | HR (bpm) | MAP (mmHg) |
| Cts-$RuCl_2(DMSO)_4$ (negative control) | 257 ± 7 | 80 ± 2 | 255 ± 6 | 82 ± 4 | 256 ± 8 | 79 ± 5 | 256 ± 9 | 81 ± 4 |
| $Ru(CO)_3$Cl(glycinate) (CO-RM-3) | 270 ± 20 | 79 ± 2 | 276 ± 20 | 73 ± 2 | 261 ± 22 | 72 ± 7 | 253 ± 23 | 65 ± 4* |

J. Effect of $Ru(CO)_3$Cl(glycinato) on Cardiac Transplant Rejection in Mice

Hearts from male BALB/c mouse (25-30 g) were used as donor organs for transplantation into male CBA mice (25-30 g). Mice were housed in groups of 3 in cages under a 12 h cycle of day/night, with free access to drinking water and fed ad libitum. All surgical procedures were performed in compliance with U.K. Home Office regulations. Animals were anaesthetized by an intraperitoneal injection of ketamine/xylazine during all procedures. The surgical technique involved the transplantation of the cardiac allograft into the recipient's neck as previously described (51). Graft survival was assessed daily by palpation, and rejection was diagnosed by cessation of ventricular contractions.

Figure 10:
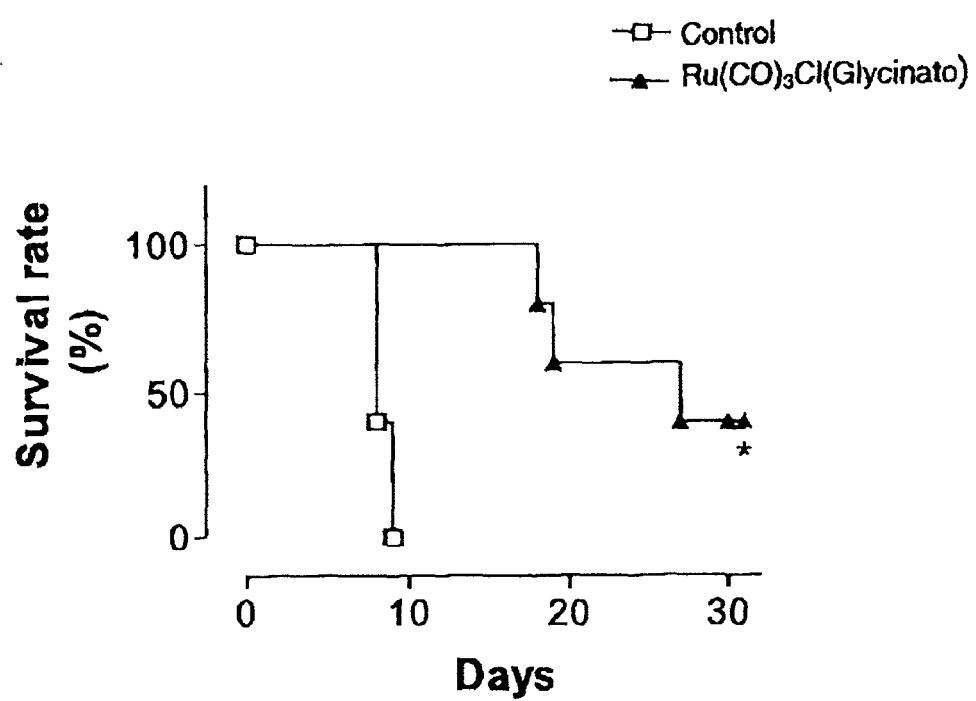
FIG. 10 is a graph showing survival rates in a transplant rejection study described below.

$Ru(CO)_3$Cl(glycinato) was dissolved in 0.1 ml saline and administered intraperitoneally. All doses are 40 mg/kg of $Ru(CO)_3$Cl(glycinato). The donors received two doses of $Ru(CO)_3$Cl(glycinato) respectively at 1 day and 15 min prior to cardiac harvest. The recipients received doses of $Ru(CO)_3$Cl(glycinato) at 1 day before surgery, 30 min prior to cardiac reperfusion and 1 h after transplantation (Day 0). Thereafter, graft recipients received a daily dose of $Ru(CO)_3$Cl(glycinato) from day 1 to day 8(inclusive) post-transplant. In the control group, recipients received an equivalent dose of saline (vehicle) 1 day before and each day (days 1 to 8) after cardiac transplantation. Carprofen (0.01 mg) was given subcutaneously for pain relief immediately after transplantation to all animals. The results of this study are shown in FIG. 10. n=5 for each group. *$p<0.002$ vs. control. BALE/c hearts transplanted into CBA mice following treatment with saline (control group) underwent rejection'very rapidly. 100% of hearts stopped beating within 9 days of transplantation. In contrast, the survival time of hearts transplanted into mice receiving $Ru(CO)_3$Cl(glycinato) was significantly prolonged ($p<0.002$) with 100% of hearts still beating 18 days after transplantation. At 25 days after heart transplantation, 60% of mice treated with $Ru(CO)_3$Cl(glycinato) still did not show any sign of rejection ($p<0.002$) and at 30 days 40% of transplanted hearts were still viable. These data demonstrate that $Ru(CO)_3$Cl(glycinato) is very effective in prolonging the survival of murine cardiac grafts and attenuating organ rejection. The result is in parallel with recently published reports showing that mice treated with CO gas (by inhalation) are significantly less susceptible to graft rejection in a model of mouse-to-rat cardiac transplant (51).

Based on the findings above on CO release and vasorelaxation, the data in this section indicates that CO liberated from the carbonyl complex mediates the anti-rejection process.

K. Effect of $Ru(CO)_3$Cl(glycinato) on Nitric Oxide Production in Macrophages Following Endotoxin Challenge The signaling molecule nitrogen monoxide (NO), which is generated in mammals by a family of constitutive (nNOS and eNOS) and inducible (iNOS) NO synthase enzymes, plays an essential regulatory role in a variety of physiological and pathophysiological processes that take place within the cardiovascular, nervous and immune systems (52). Overproduction of NO has been established as a potent cytotoxic weapon in host defense against infection, inflammation and cancer. Considerable amounts of NO can originate from activated iNOS when appropriately induced by cytokines, endotoxins or lipopolysaccharide (LPS), oxygen free radicals or other stressful stimuli (53). In particular, macrophages are a specific target of pro-inflammatory stimuli as they highly express iNOS and can generate excessive amounts of NO to modulate important cytostatic/bactericidal actions. From unpublished data, it has been postulated that induction of the heme oxygenase-1 (HO-1)/bilirubin/CO pathway represents a counter-regulatory System against the deleterious effects elicited by overproduction of NO. Specifically, both CO and bilirubin may interfere with NO generation by acting as inhibitors of NOS activity and scavenger of NO, respectively. CO gas has been shown to inhibit NOS activity in various tissues (54), and it has been suggested that bilirubin can directly interact with NO and NO-related species (55).

Figure 11:
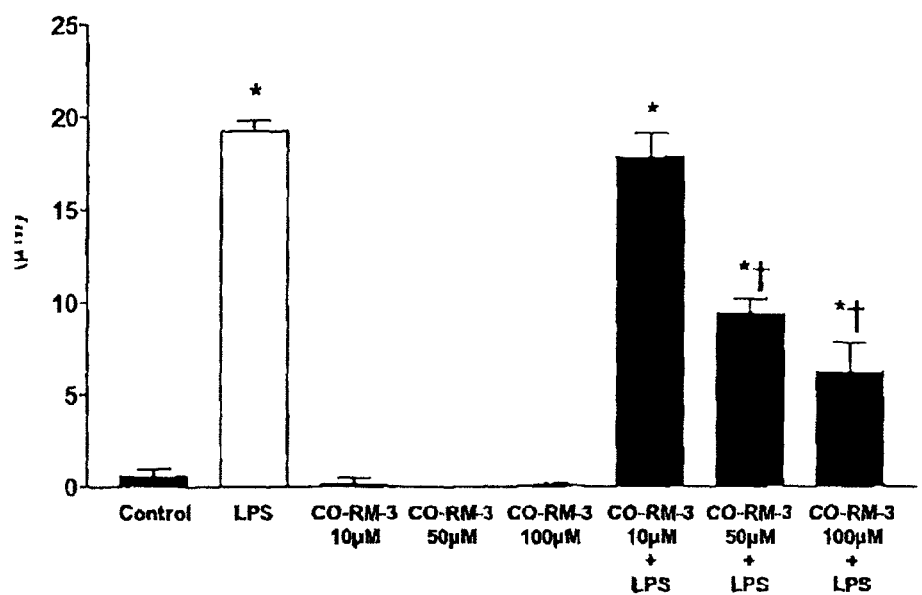
FIG. 11 is a graph of nitrite produced in a study of NO production in macrophages described below.
Figure 12:
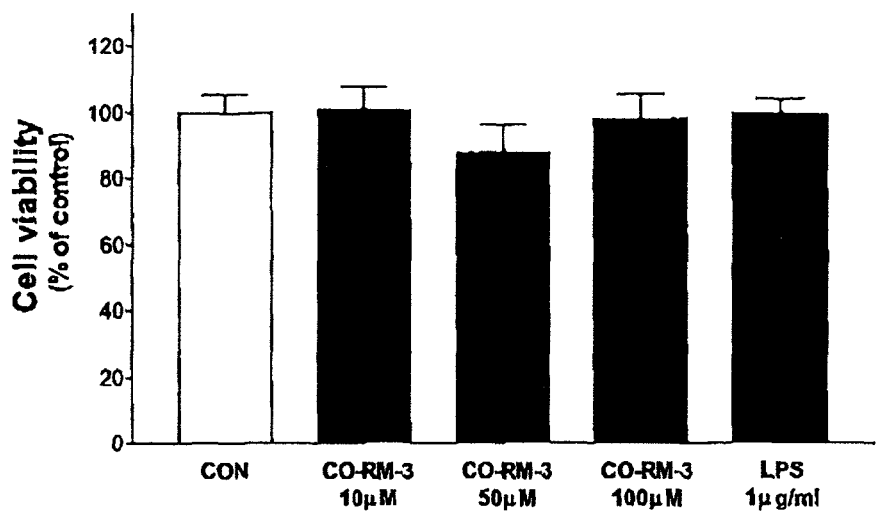
FIG. 12 is graphs of cell viability in the study of NO production in macrophages.
Figure 12:
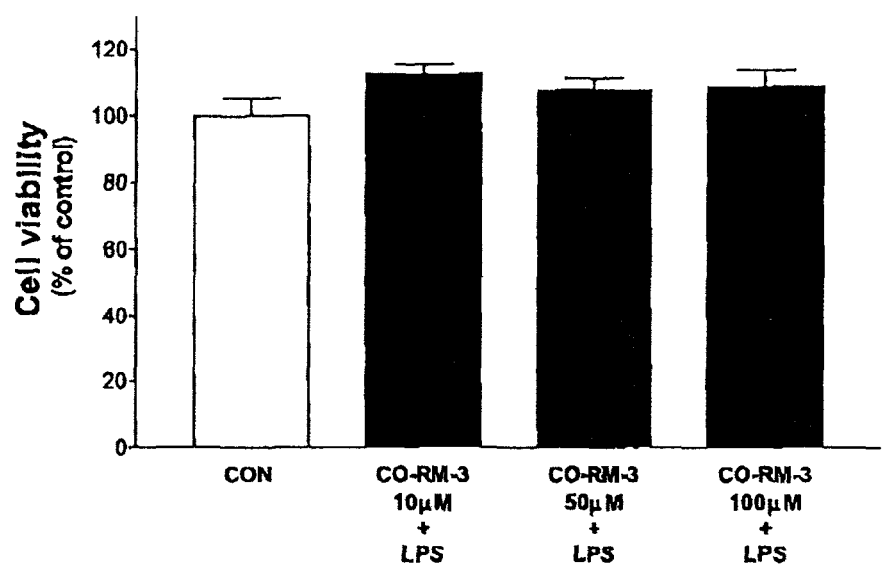

The present study was undertaken to assess the effect of $Ru(CO)_3Cl(glycinato)$ (CO-RM-3) on the production of NO from endotoxin-stimulated macrophages. Mouse RAW 264.7 macrophages were cultured in 24 wells using DMEM medium Confluent cells were incubated for 24 h with *E. Coli* lipopolysaccharide (LPS, 3 µg/ml) in the presence or absence of increasing concentrations of CO-RM-3 (10, 50 and 100 µM). Control cells were exposed to culture medium alone. Nitrite in the culture medium was measured as an index of NO production using the Griess reagent method (56). Cell viability was also assessed in macrophages 24 h after treatment with the various agents as described in reference 47. Treatment of macrophages with LPS caused a significant increase in nitrite levels ($p<0.05$) after 24 h incubation (see FIG. 11, where bars represent the mean±S.E.M. of 6 independent experiments. *$p<0.05$ vs. control; +$p<0.05$ vs. LPS. The presence of CO-RM-3 significantly attenuated nitrite generation in a concentration dependent manner. As shown in FIG. 12 (where bars represent the mean±S.E.M. of 6 independent experiments), these treatments did not affect cell viability as no toxic effect was observed at the end of the incubation period.

These data indicate in the ability of CO released from CO-RM-3 to prevent the inflammatory response in macrophages by inhibiting the production of iNOS-derived NO. Furthermore, and in line with the beneficial effects shown by CO-RM-3 on blood pressure and cardiac graft rejection, these results suggest a potential therapeutic application of water-soluble CO carriers in the modulation of vascular- and inflammatory-related pathological states.

L. Syntheses

Synthetic methods for obtaining compounds of FIGS. 9*a* to 9*f* tested for CO release will now be described.

Purity of the product has not been investigated in detail. Stereoisomers are expected to be present.

Preparation of $Ru(CO)_3Cl\ (NH_2CH_2\{CH_2SH\}CO_2)$ $[M_R\ 340.5]$
L-Cysteine complex. Reference number: CO-RM-26

$[Ru(CO)_3Cl_2]_2$ (0.129 g, 0.25 mmol) and L-cysteine (0.039 g, 0.50 mmol) were placed under nitrogen in a round bottomed flask. Methanol (75 cm³) and sodium ethoxide (0.034 g, 0.50 mmol) were added and the reaction allowed to stir for 18 hours. The solvent was then removed under pressure and the yellow residue redissolved in THF, filtered and excess 40-60 light petroleum added. The yellow solution was evaporated down to given an orange solid (0.120 g, 70%).

Preparation of $Ru(CO)_3Cl\ (NH_2CH_2CO2)$ $[M_R\ 294.5]$
Glycine complex. Reference number: CO-RM-3

$[Ru(CO)_3Cl_2]_2$ (0.129 g, 0.25 mmol) and glycine (0.039 g, 0.50 mmol) were placed under nitrogen in a round bottomed flask. Methanol (75 cm³) and sodium ethoxide (0.034 g, 0.50 mmol) were added and the reaction allowed to stir for 18 hours. The solvent was then removed under pressure and the yellow residue redissolved in THF, filtered and excess 40-60 light petroleum added. The yellow solution was evaporated down to give a pale yellow solid (0.142 g, 96%).

Preparation of $Ru(CO)_3Cl\ (NH_2CH\{CHMeCH_2CH_3\}CO_2)$ $[M_R\ 350.5]$
DL-Isoleucine complex. Reference number: CO-RM-38

$[Ru(CO)_3Cl_2]_2$ (0.129 g, 0.25 mmol) and DL-isoleucine (0.066 g, 0.50 mmol) were placed under nitrogen in a round bottomed flask. Methanol (75 cm³) and sodium ethoxide (0.034 g, 0.50 mmol) were added and the reaction allowed to stir for 18 hours. The solvent was then removed under pressure and the yellow residue redissolved in THF, filtered and excess 40-60 light petroleum added. The yellow solution was evaporated down to give a yellow solid (0.086 g, 49%).

Preparation of $Ru(CO)_3Cl\ (NH_2CH\{CH_2OH\}CO_2)$ $[M_R\ 324.5]$
L-Serine complex. Reference number: CO-RM-39.

$[Ru(CO)_3Cl_2]_2$ (0.129 g, 0.25 mmol) and L-serine (0.053 g, 0.50 mmol) were placed under nitrogen in a round bottomed flask. Methanol (75 cm³) and sodium ethoxide (0.034 g, 0.50 mmol) were added and the reaction allowed to stir for 18 hours. The solvent was then removed under pressure and the yellow residue redissolved in THF, filtered and excess 40-60 light petroleum added. The yellow solution was evaporated down to give a pale yellow solid (0.095 g, 59%)

Preparation of $Ru(CO)_3Cl\ (NH_2CH\{CH_3\}CO_2$ $[M_R\ 308.5]$
L-Alanine complex. Reference number: CO-RM-40.

$[Ru(CO)_3Cl_2]_2$ (0.129 g, 0.25 mmol) and L-alanine (0.045 g, 0.50 mmol) were placed under nitrogen in a round bottomed flask. Methanol (75 cm³) and sodium ethoxide (0.034 g, 0.50 mmol) were added and the reaction allowed to stir for 18 hours. The solvent was then removed under pressure and the yellow residue redissolved in THF, and filtered. The solution was evaporated down to give an orange solid (0.145 g, 94%).

Preparation of $Ru(CO)_3Cl\ (NH_2CH(CH_2CH_2CONH_2)CO_2)$ $[M_R\ 365.5]$
L-Glutamine complex. Reference number: CO-RM-42.

$[Ru(CO)_3Cl_2]_2$ (0.129 g, 0.25 mmol) and L-glutamine (0.073 g, 0.50 mmol), were placed under nitrogen in a round bottomed flask. Methanol (75 cm³) and sodium ethoxide (0.034 g, 0.50 mmol) were added and the reaction allowed to stir for 18 hours. The solvent was then removed under pressure and the yellow residue redissolved in THF and filtered. The solution was evaporated down to give a yellow oil which solidified under high vacuum to give a pale yellow solid (0.170 g, 93%).

Preparation of $RU\ (CO)_3Cl\ (NH_2CH\{CH_2CH_2NHC(=NH)NH_2\}CO_2)$ $[M_R\ 393.5]$
L-Arginine complex. Reference number: CO-RM-43.

$[Ru(CO)_3Cl_2]_2$ (0.129 g, 0.25 mmol) and L-arginine (0.087 g, 0.50 mmol): were placed under nitrogen in a round bottomed flask. Methanol (75 cm³) and sodium ethoxide (0.034 g, 0.50 mmol) were added and the reaction allowed to stir for 18 hours. The solvent was then removed under pressure and the yellow residue redissolved in THF/MeOH (4:1) and filtered. The solution was evaporated down to given an orange solid (0.185 g, 94%).

Preparation of Ru(CO)$_3$Cl (NH$_2$CH{CH$_2$CH$_2$CH$_2$CH$_2$NH$_2$}CO$_2$) [$M_R$ 365.5] L-Lysine complex. Reference number: CO-RM-46.

[Ru(CO)$_3$Cl$_2$]$_2$ (0.129 g, 0.25 mmol) and L-lysine (0.073 g, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF/MeOH (3:1) and filtered. The solution was evaporated down to give a yellow oil which solidified under high vacuum to given an orange solid (0.163 g, 89%).

Preparation of Ru(CO)$_3$Cl (NH$_2$CH{CH(CH$_3$)$_2$}CO$_2$[$M_R$ 336.5]
L-Valine complex. Reference number: CO-RM-67.

[Ru(CO)$_3$Cl$_2$]$_2$ (0.129 g, 0.25 mmol) and L-valine (0.059 g, 0.50 mmol) were placed under nitrogen in a round bottomed flask. Methanol (75 cm$^3$) and sodium ethoxide (0.034 g, 0.50 mmol) were added and the reaction allowed to stir for 18 hours. The solvent was then removed under pressure and the yellow residue redissolved in THF and filtered. Excess 40-60 light petroleum was added and the solution evaporated down to given a white solid'(0.114 g, 68%).

Preparation of Ru(CO)$_3$Cl (NH$_2$CH{CH(OH)CH$_3$}CO$_2$) [$M_R$ 338.5]
L-Threonine complex Reference number: CO-RM-74.

[Ru(CO)$_3$Cl$_2$]$_2$ (0.129 g, 0.25 mmol) and L-threonine (0.060 g, 0.50 mmol) were placed under nitrogen in a round bottomed flask. Methanol (75 cm$^3$) and sodium ethoxide (0.034 g, 0:50 mmol) were added and the reaction allowed to stir for 18 hours. The solvent was then removed under pressure and the yellow residue redissolved in THF and filtered. Excess 40-60 light petroleum was added and the solution evaporated down to give a white solid 0.149 g, 88%).

Preparation of [Fe(η-C$_5$H$_5$)(CO)$_3$]Cl [$M_R$ 240.5]
Reference number: CO-RM-70.

A sodium amalgam was prepared by, under nitrogen in a Schlenk tube, dissolving sodium metal (2.04 g) in mercury (18 cm$^3$). This was allowed to cool to room temperature and tetrahydrofuran (40 cm$^3$) added. Then [FeCp(CO)$_2$]$_2$ (7.08 g, 20.3 mmol) in tetrahydrofuran (60 cm$^3$) added and the flask shaken vigorously for 45 minutes.

Then into a large 3-necked flask purged with nitrogen, THF (300 cm$^3$) and ethyl chloroformate (40 mmol, 4.34 g, 3.84 cm$^3$) were placed and cooled to 0° C. The red-yellow solution of cleaved dimer was then transferred into the round bottomed flask and allowed to stir for one hour at low temperature before being concentrated in volume. The red-brown residue was extracted with benzene (5×20 cm$^3$), the extracts filtered, and HCl gas blown through the solution for 15 minutes. An immediate precipitation was observed, the solution was reduced in volume and the orange precipitate collected, washed with diethyl ether (20 cm$^3$) and dried. (4.84 g, 50%).

Preparation of [Fe(η-C$_5$H$_5$)(CO)$_3$]PF$_6$[$M_R$ 350]
Reference number: CO-RM-71.

[Fe(η-C$_5$H$_5$)(CO)$_3$]Cl (3.00 g, 12.5 mmol) was dissolved in water (50 cm$^3$) and sodium hexafluorophosphate (2.00 g, 1eq) in water (50 cm$^3$) added. An orange precipitate was immediately formed, the reaction stirred for 15 minutes and the orange precipitate collected under suction (3.04 g, 70%).

Preparation of Ru(CO)$_3$Cl$_2$(guanosine) [$M_R$ 540]
Reference number: CO-RM-17.

[Ru(CO)$_3$Cl$_2$]$_2$ (0.129 g, 0.25 mmol) and guanosine (0.142 g, 0.50 mmol) were placed under nitrogen in a round bottomed flask. Methanol (75 cm$^3$) was added and the reaction allowed to stir for 18 hours. The solution was then filtered and reduced in volume to approximately 10 cm$^3$. Excess diethyl ether was added and the white precipitate formed allowed to settle out in the freezer overnight. The solvent was pipetted off to leave a white solid which was dried under high vacuum (0.130 g, 48%).

Preparation of [Ru(CO)$_3$Cl (guanosine)$_2$]/Cl [$M_R$ 824]
Reference number: CO-RM-18.

[Ru(CO)$_3$Cl$_2$]$_2$ (0.129 g, 0.25 mmol) and guanosine (0.284 g, 1.00 mmol) were placed under nitrogen in a round bottomed flask. Methanol (75 cm$^3$) was added and the reaction allowed to stir for 18 hours. The solution was then filtered and reduced in volume to approximately 10 cm$^3$. Excess diethyl ether was added and the white precipitate formed allowed to settle out in the freezer overnight. The solvent was pipetted off to leave a white solid which was dried under high vacuum (0.220 g, 53%).

Preparation of Ru(CO)$_3$Cl$_2$(triacetyl-guanosine) [$M_R$ 666]
Reference number: CO-RM-29.

[Ru(CO)$_3$Cl$_2$]$_2$ (0.129 g, 0.25 mmol) and 2, 3, 5-triacetylguanosine (0.205 g, 0.50 mmol) were placed under nitrogen in a round bottomed flask. Methanol (75 cm$^3$) was added and the reaction allowed to stir for 18 hours. The solution was then filtered and reduced in volume to approximately 10 cm$^3$. Excess diethyl ether was added and the white precipitate formed allowed to settle out in the freezer overnight. The solvent was pipetted off to leave a white solid which was dried under high vacuum (0.212 g, 63%).

Preparation of Ru(CO)$_3$Cl$_2$(guanine) [$M_R$ 408]
Reference number: CO-RM-22.

[Ru(CO)$_3$Cl$_2$]$_2$ (0.129 g, 0.25 mmol) and guanine (0.076 g, 0.50 mmol) were placed under nitrogen in a round bottomed flask. Tetrahydrofuran (75 cm$^3$) was added and the reaction allowed to stir for 18 hours. The solution was then reduced in volume to approximately 10 cm$^3$. Excess 40-60 light petroleum was added and the precipitate formed allowed to settle out in the freezer overnight. The solvent was pipetted off to leave a pale yellow solid which was dried under high vacuum (0.082 g, 39%).

Preparation of [Ru(CO)$_3$Cl (guanine)$_2$]Cl [$M_R$ 558]
Reference number: CO-RM-23.

[Ru(CO)$_3$Cl$_2$]$_2$ (0.129 g, 0.25 mmol) and guanine (0.152 g, 1.00 mmol) were placed under nitrogen in a round bottomed flask. Tetrahydrofuran (75 cm$^3$) was added and the reaction allowed to stir for 18 hours. The solution was then reduced in volume to approximately 10 cm$^3$. Excess 40-60 light petroleum was added and the precipitate formed allowed to settle out in the freezer overnight. The solvent was pipetted off to leave a cream solid which was dried under high vacuum (0.170 g, 61%).

Preparation of fac-RuCl$_2$(CO)$_3$(THF)[$M_R$ 329]
Reference number: CO-RM-11.

[Ru(CO)$_3$Cl$_2$]$_2$ (0.380 g, 0.74 mmol) and tetrahydrofuran (5 cm$^3$) were placed in a conical flask and the yellow solution stirred for 15 minutes. Then the solvent was removed under reduced pressure leaving a yellow oil which upon standing solidified. Addition of diethylether (20 cm$^3$) accompanied by sonication afforded a white precipitate and yellow solution. The solid was collected and dried under vacuum (0.134 g, 28%).

Preparation of [RuCl$_2$(CO)$_2$]$_n$ [$M_R$ Unknown]
Reference number: CO-RM-10.

RuCl$_3$xH$_2$O (5.00 g), concentrated hydrochloric acid (25 cm$^3$) and formic acid (25 cm$^3$) were placed in a 3-necked round bottomed flask and the mixture refluxed for 18 hours. The clear yellow solution was then reduced in volume to leave a yellow/orange precipitate, which was transferred into a Soxhlet thimble and extracted overnight with methanol. This solution was then reduced in volume to give an orange oil which solidified under high vacuum to afford an orange precipitate (5.30 g).

Preparation of $Ru(CO)_3(O\{CH_2CO_2\}_2)$ [$M_R$ 317]
Diglycolic acid complex. Reference number: CO-RM-99

$[Ru(CO)_3Cl_2]_2$ (0.129 g, 0.25 mmol) and diglycolic acid (0.067 g), 0.50 mmol) were placed under nitrogen in a round bottomed flask. Methanol (75 cm$^3$) and sodium ethoxide (0.068 g, 1.00 mmol) were added and the reaction allowed to stir for 18 hours. The solvent was then removed under pressure and the yellow residue redissolved in THF, filtered and excess 40-60 light petroleum added. The yellow solution was evaporated down to give a white solid (0.142 g, 85%).

Preparation of $Ru(CO)_3(NH\{CH_2CO_2\}_2)$ [$M_R$ 317]
Iminodiacetic acid complex. Reference number: CO-RM-97

$[Ru(CO)_3Cl_2]_2$ (0.129 g, 0.25 mmol) and iminodiacetic acid (0.066 g, 0.50 mmol) were placed under nitrogen in a round bottomed flask. Methanol (75 cm$^3$) and sodium ethoxide (0.068 g, 1.00 mmol) were added and the reaction allowed to stir for 18 hours. The solvent was then removed under pressure and the yellow residue redissolved in THF/MeOH (4:1), filtered and excess 40-60 light petroleum added. The yellow solution was evaporated down to give an off-white solid (0.140 g, 89%).

Syntheses suitable for CO-RM-1a, CO-RM-1b and the negative controls for these compounds are in reference 57. Synthesis of CO-RM-16 is found in reference 58.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

REFERENCES

1. Piantadosi C A. Toxicity of carbon monoxide: hemoglobins vs. histotoxic mechanisms. In: *Carbon monoxide*. (Edited by Penney D G). 1996; Chapter 8.
2. Sjostrand T. Endogenous formation of carbon monoxide in man under normal and pathological conditions. Scan J Clin Lab Invest 1949; 1:201-14.
3. Coburn R F, Blakemore W S, Forster R E. Endogenous carbon monoxide production in man. J Clin Invest 1963; 42:1172-6.
4. Coburn R F, Williams W J, Forster R E. Effect of erythrocyte destruction on carbon monxide production in man. J Clin Invest 1964; 43:1098-103.
5. Coburn R F, Williams W J, Kahn S B. Endogenous carbon monoxide production in patients with hemolytic anemia. J Clin Invest 1966; 45:460-8.
6. Sjostrand T. The formation of carbon monoxide by in vitro decomposition of haemoglobin in bile pigments. Acta Physiol Scand 1952; 26:328-33.
7. Coburn R F, Williams W J, White P, Kahn S B. The production of carbon monoxide from hemoglobin in vivo. J Clin Invest 1967; 46:346-56.
8. Tenhunen R, Marver H S, Schmid R. Microsomal heme oxygenase. Characterization of the enzyme. J Biol Chem 1969; 244:6388-94.
9. Scharf S M, Permutt S, Bromberger-Barnea B. Effects of hypoxic and CO hypoxia on isolated hearts. J Appl Physiol 1975; 39:752-8.
10. Shibahara S, Muller R, Taguchi H, Yoshida T. Cloning and expression of cDNA for rat heme oxygenase. Proc Natl Acad Sci USA 1985; 82:7865-9.
11. Maines M D, Trakshel G M, Kutty R K. Characterization of two constitutive forms of rat liver microsomal heme oxygenase; only one molecular species of the enzyme is inducible. J Biol Chem 1986; 261:411-9.
12. Cruse I, Maines M D. Evidence suggesting that the two forms of heme oxygenase are products of different genes. J Biol Chem 1988; 263:3348-53.
13. Trakshel G M, Maines M D. Multiplicity of heme oxygenase isozymes: HO-1 and HO-2 are different molecular species in rat and rabbit. J Biol Chem 1989; 264:1323-8.
14. Maines M D. Heme oxygenase: function, multiplicity, regulatory mechanisms, and clinical applications. FASEB J 1988; 2:2557-68.
15. Marks G S, Brien J F, Nakatsu K, McLaughlin B E. Does carbon monoxide have a physiological function? Trends Pharmacol Sci 1991; 12:185-8.
16. Stocker R, Yamamoto Y, McDonagh A F, Glazer A N, Ames B N, Bilirubin is an antioxidant of possible physiological importance. Science 1987; 235:1043-6.
17. McDonagh A F. Is bilirubin good for you. Clin Perinat 1990; 17:359-69.
18. Coceani F, Hamilton N C, Labuc J, Olley P M. Cytochrome P 450-linked monooxygenase: involvement in the lamb ductus arteriosus. Am J Physiol 1984; 246(4 Pt 2):H640-3.
19. Vedernikov I P, Graser T, Vanin A F. Similar endothelium-independent arterial relaxation by carbon monoxide and nitric oxide. Biomed Biochim Acta 1989; B:601-3.
20. Furchgott R F, Jothianandan D. Endothelium-dependent and -independent vasodilation involving cGMP: relaxation induced by nitric oxide, carbon monoxide and light. Blood Vessels 1991; 28:52-61.
21. Morita T, Perrella M A, Lee M E, Kourembanas S. Smooth muscle cell-derived carbon monoxide is a regulator of vascular cGMP. Proc Natl Road Sci USA 1995; 92:1475-9.
22. Christodoulides N, Durante W, Kroll M H, Schafer A I. Vascular smooth muscle cell heme oxygenases generate guanylyl cyclase-stimulatory carbon monoxide. Circulation 1995; 91:2306-9.
23. Sammut I A, Foresti R, Clark J E, Exon D J, Vesely M J J, Sarathchandra P, Green C J, Motterlini R. Carbon monoxide is a major contributor to the regulation of vascular tone in aortas expressing high levels of haeme oxygenase-1. Br J Pharmacol 1998; 125:1437-44.
24. Coceani F. Carbon monoxide in vasaregulation: the promise and the challenge. Circ Res 2000; 86(12):1184-6.
25. Feelisch M. The biochemical pathways of nitric-oxide, formation from nitrovasodilators: appropriate choice of exogenous NO donors and aspects of preparation and handling of aqueous NO solutions. J Cardiovasc Pharmacol 1991; 17:S 25-33.
26. Feelisch M. The use of nitric oxide donors in pharmacological studies. Naunyn-Schmiedeberg's Arch Pharmacol 1998; 358:113-22.
27. Luscher T F. Endogenous and exogenous nitrates and their role in myocardial ischaemia. Br J din Pharmacol 1992; 34 Suppl 1:29 S-35S.
28. Saavedra J E, Billiar T R, Williams D L, Kim Y M, Watkins S C, Keefer L K. Targeting nitric oxide (NO) delivery in vivo. Design of a liver-selective NO donor prodrug that blocks tumor necrosis factor-alpha-induced apoptosis and toxicity in the liver. J Med Chem 1997; 40(13):1947-54.

29. Saavedra J E, Southan G J, Davies K M, Lundell A, Markou C, Hanson S R, Adrie C, Hurford W E, Zapol W M, Keefer L K. Localizing antithrombotic and vasodilatory activity with a novel, ultrafast nitric oxide donor. J Med Chem 1996; 39(22):4361-5.

30. Abraham N G, Drummond G S, Lutton J D, Kappas A. The biological significance and physiological role of heme oxygenase. Cell Physiol Biochem 1996; 6:129-68.

31. Foresti R, Motterlini R. The heme oxygenase pathway and its interaction with nitric oxide in the control of cellular homeostasis. Free Rad Res 1999; 31:459-75.

32. Maines M D. The heme oxygenase system: a regulator of second messenger gases. Annu Rev Pharmacol Toxicol 1997; 37:517-54.

33. Soares M P, Lin Y, Anrather J, Csizmadia E, Takigami K, Sato K, Grey S T, Colvin R P, Choi A M, Poss K D, et al. Expression of heme oxygenase-1 can determine cardiac xenograft survival. Nature Med 1998; 4:1073-7.

34. Hancock W W, Buelow R, Sayegh M H, Turka L A, Antibody-induced transplant arteriosclerosis is prevented by graft expression of anti-oxidant and anti-apoptotic genes. Nature Med 1998; 4:1392-6.

35. Clark J E, Foresti R, Sarathchandra P, Kaur H, Green C J, Motterlini R. Herne oxygenase-1-derived bilirubin ameliorates post-ischemic myocardial dysfunction. Am J Physiol Heart Ciro Physiol 2000; 278:H643-51.

36. Willis D, Moore A R, Frederick R, Willoughby D A. Heme oxygenase: a novel target for the modulation of inflammatory response. Nature Med 1996; 2:87-90.

37. Bauer M, Pannen B H J, Bauer I, Herzog C, Wanner G A, Hanselmann R, Zhang J X, Clemens M G, Larsen R. Evidence for a functional-link between stress-response and vascular control in hepatic portal circulation. Am J Physiol 1996; 271:G929-35.

38. Fukuda K, Panter S S, Sharp F R, Noble L J. Induction of heme oxygenase-1 (HO-1) after traumatic brain injury in the rat. Neurosci Lett 1995; 199:127-30.

39. Yet S F, Pellacani A, Patterson C, Tan L, Folta S C, Foster L, Lee W S, Hsieh C M, Perrella M A. Induction of heme oxygenase-1 expression in vascular smooth muscle cells. A link to endotoxic shock. J Biol Chem 1997; 272:4295-301.

40. Motterlini R, Gonzales A, Foresti R, Clark J E, Green C J, Winslow RM. Heme oxygenase-1-derived carbon monoxide contributes to the suppression of acute hypertensive responses in vivo. Circ Res 1998; 83:568-77.

41. Otterbein L E, Mantell L L, Choi A M K. Carbon monoxide provides protection against hyperoxic lung injury. Am J Physiol 1999; 276:L688-94.

42. Otterbein L E, Kolls J K, Mantell L L, Cook J L, Alam J, Choi A M K. Exogenous administration of heme oxygenase-1 by gene transfer provides protection against hyperoxia-induced lung injury. J Clin Invest 1999; 103:1047-54.

43. Otterbein L E, Bach F H, Alam J, Soares M, Tao Lu H, Wysk M, Davis R J, Flavell R A, Choi A M. Carbon monoxide has anti-inflammatory effects involving the mitogen-activated protein kinase pathway. Nat Med 2000; 6(4):422-8.

44. Engelking P C, Lineberger W C. Laser photoelectron spectrometry of the negative ions of iron and iron carbonyls. Electron affinity determination for the series $Fe(CO)_n$, n=0, 1, 2, 3, 4. J Am Chem Soc 1979; 101:5569-73.

45. Herrick R S, Brown T L. Flash photolytic investigation of photoinduced carbon monoxide dissociation from dinuclear manganese carbonyl compounds. Inorg Chem 1984; 23:4550-3.

46. Alessio E, Milani B, Bolle M, Mestroni G, Falechini P, Todone F, Geremia S, Calligaris M. Carbonyl derivatives of chloride-dimethyl sulfoxide-ruthenium(II) complexes: synthesis, structural characterization, and reactivity of $Ru(CO)_x(DMSO)_{4-x}Cl_2$ complexes (x=1-3). Inorg Chem 1995; 34:4722-34.

47. Clark J E, Foresti R, Green C J, Motterlini R. Dynamics of haem oxygenase-1 expression and bilirubin production in cellular protection against oxidative stress. Biochem J 2000; 348:615-9.

48. Vanin A F. Dinitrosyl iron complexes and S-nitrosothiols are two possible forms for stabilization and transport of nitric oxide in biological systems. Biochemistry (Moscow) 1998; 63(7):782-93.

49. Chomczynski P, Sacchi N. Single step method of RNA isolation by acid guanidinium thiocyanate-phenol-chloroform extraction. Anal Biochem 1987; 162:156-9.

50. Motterlini R, Foresti R, Bassi R, Calabrese V, Clark J E, Green C J. Endothelial heme oxygenase-1 induction by hypoxia: modulation by inducible nitric oxide synthase (iNOS) and S-nitrosothiols. J Biol Chem 2000; 275:13613-20.

51. Sato K., Balla J., Otterbein L., Smith R. N., Brouard S., Lin Y., Csizmadia E., Sevigny J., Robson S. C., Vercellotti G., Choi A. M., Bach F. H., Soares M. P. Carbon monoxide generated by heme oxygenase-1 suppresses the rejection of mouse-to-rat cardiac transplants. *J. Immunol.* 166:4185-4194, 2001.

52. Moncada S, Palmer R M J, and Higgs E A. Nitric oxide: physiology, pathophysiology, and pharmacology. *Pharmacol Rev* 43: 109-142, 1991.

53. Nathan C. Inducible nitric oxide synthase: what difference does it make? *J Clin Invest* 100: 2417-2423, 1997.

54. White K A et al. Biochemistry 31: 6627-6631, 1992.

55. Kaur H, Green C J and Motterlini R. Interaction of bilirubin and biliverdin with reactive nitrogen species. *Free Rad. Biol. Med.* 27:S78, 1999.

56. Foresti R, Clark J, Green C J, and Motterlini R. Thiol compounds interact with nitric oxide in regulating heme oxygenase-1 induction in the endothelium. Involvement of superoxide and peroxynitrite anions. *J. Biol. Chem.* 272: 18411-18417, 1997.

57. G. Pneumatakakis, A. Yannopoulos and J. Markopoulos, *Inorg. Chim. Acta,* 1988, 151, 243.

58. E. Alessio, B. Milani, M. Bone, G. Mestroni, P. Faleschini, F, Todone, S. Geremia and M. Calligaris, *Inorg. Chem.,* 1995, 34, 4722.

We claim:

1. A method of treatment of a viable mammalian organ extracorporeally comprising contacting the organ with a metal carbonyl, wherein the metal carbonyl makes available CO suitable for physiological effect.

2. A method of treatment of a viable mammalian organ extracorporeally during storage and/or transport of an organ for transplant surgery comprising contacting the organ with a metal carbonyl, wherein the metal carbonyl makes available CO suitable for physiological effect.

3. A method according to claim 1, wherein the metal carbonyl is in dissolved form.

4. A method according to claim 3, wherein the metal carbonyl is in aqueous solution.

5. A method according to claim 2 and wherein the metal carbonyl is in dissolved form.

6. A method according to claim 5, wherein the metal carbonyl is in aqueous solution.

7. A method of treatment of a viable mammalian organ extracorporeally comprising contacting the organ with a metal carbonyl, wherein the metal carbonyl makes available CO suitable for physiological effect, and wherein the metal carbonyl is a compound of the formula $M(CO)_xA_y$ where x is at least one, y is at least one, M is a metal, the or each A is an atom or group bonded to M by an ionic, covalent or coordination bond, and in the case where y>1 each A may be the same or different, or a pharmaceutically acceptable salt of such a compound.

8. A method according to claim 7, wherein M is a transition metal.

9. A method according to claim 7, wherein A is selected from halogens, groups having N, P, O or S atoms providing lone electron pairs for coordination bonding to M, and conjugated carbon groups.

10. A method of treatment of a viable mammalian organ extracorporeally, comprising contacting the organ with a metal carbonyl, wherein the metal carbonyl makes available CO suitable for physiological effect, whereby the treatment causes vasodilation.

11. A method according to claim 8, wherein A is selected from halogens, groups having N, P, O or S atoms providing lone electron pairs for coordination bonding to M, and conjugated carbon groups.

* * * * *